(12) United States Patent
Vollert et al.

(10) Patent No.: US 8,026,069 B2
(45) Date of Patent: Sep. 27, 2011

(54) PROCESS FOR IDENTIFICATION OF COMPOUNDS FOR MODULATING THE ACTIVITY OF SODIUM/CALCIUM EXCHANGE TRANSPORTER

(75) Inventors: Henning Vollert, Hofheim-Lorsbach (DE); Sven Geibel, Darmstadt (DE); Bela Kelety, Frankfurt am Main (DE); Wolfgang Doerner, Hochheim (DE); Andreas Haase, Frankfurt (DE); Natalie Watzke, Weinheim (DE); Kerstin Diekert, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 730 days.

(21) Appl. No.: 11/573,762

(22) PCT Filed: Aug. 10, 2005

(86) PCT No.: PCT/EP2005/008660
§ 371 (c)(1),
(2), (4) Date: Jan. 16, 2008

(87) PCT Pub. No.: WO2006/018197
PCT Pub. Date: Feb. 23, 2006

(65) Prior Publication Data
US 2008/0211485 A1    Sep. 4, 2008

(30) Foreign Application Priority Data
Aug. 19, 2004    (EP) .................................... 04019635

(51) Int. Cl.
*G01N 33/53*    (2006.01)
*C07K 14/00*    (2006.01)

(52) U.S. Cl. ............................................. 435/7.1; 514/2

(58) Field of Classification Search ........................ None
See application file for complete search history.

(56) References Cited

FOREIGN PATENT DOCUMENTS
WO    WO 02/074983    9/2002

OTHER PUBLICATIONS

Cahalan and Neher, "Patch Clamp Techniques: An Overview", Methods in Enzymology 207: 3-14 (1992).*
Eisenrauch et al., Electrical Currents generated by a partially purified Na/Ca exchanger from lobster muscle reconstituteed into liposomes and adsorbed on black lipid membranes: activation by photolysis of Ca2+, J. Membrane Biology, vol. 145, 1995, p. 151-164.
Gaellini et al., The human SLC8A3 gene and the tissue-specific Na+/Ca2+ exchanger 3 isoforms, Gene, vol. 298, 2002, p. 1-7.
Hinata et al., Stochiometry of Na+/Ca++ exchange is 3:1 in guinea-pig ventricular myocytes, J. of Physiology, vol. 545, No. 2, 2002, pp. 453-461.
Hobai et al., the potential of Na+/Ca++ exchange blockers in the treatment of cardiac diseases, Expert Opinion Investig. Drugs, vol. 13, No. 6, Jun. 1, 2004, pp. 653-664.
Iwamoto et al., Moleclar determinates of Na+/Ca++ exchange (NCX1) inhibition by SEA0400, J. of Biological Chemistry, vol. 279, No. 9, Feb. 27, 2004, pp. 7544-7553.
Komuro et al., Molecular cloning and characterization of the human cardiac Na+/Ca2+ exchanger CDNA, PNAS, vol. 89. No. 10, 1992, p. 4769-4773.
Kofuji et al., Expression of the Na-Ca exchanger in diverse tissues: a study using the cloned human cardiac Na-Ca exchanger, Cell Physiol vol. 32, 1992, pC1241-1249.
Li et al., Cloning of the NCX2 isoform of the plasma membrane Na(+)-Ca2+ exchanger, J. Biol. Chem., vol. 269, No. 26, 1994, p. 17434-9.
Nicoll et al., Cloning of a third mammalian Na+-Ca-2+ exchanger, NCX3, J. of Biological Chemistry, Am Soc. of Biological Chemists Inc., vol. 271, No. 4, Oct. 4, 1996, pp. 24914-24921.
Nicoll et al., Molecular cloning and functional expression of the cardiac sarcolemmal Na(+)-Ca2+ exchanger, Science, vol. 250, 1990, p. 562-5.

* cited by examiner

Primary Examiner — Anand Desai

(57) ABSTRACT

The invention refers to a cell free assay for determining the activity of a $Na^+/Ca^{2+}$ exchanger (NCX) protein by means of a cell free electrophysiological sensor chip, a kit of parts comprising the sensor chip with a NCX protein as well as the manufacturing and use of the kit of parts.

27 Claims, 30 Drawing Sheets

Fig. 1 A:

| | |
|---|---|
| Names: | NCX1 (SLCA1) |
| Vector/sites: | pVL1393 XbaI/ NotI |
| Insert: | human NCX1 |
| GenBank/Embl: | NM_021097 |
| Note: | total conformity with NM_021097 |

CR231
NCX1 pVL1393
XbaI/NotI
ORF 4154-7075

```
        AAGCTTTACTCGTAAAGCGAGTTGAAGGATCATATTTAGTTGCGTTTATGAGATAAGATT
   1 ---------+---------+---------+---------+---------+---------+ 60
        TTCGAAATGAGCATTTCGCTCAACTTCCTAGTATAAATCAACGCAAATACTCTATTCTAA

GAAAGCACGTGTAAAATGTTTCCCGCGCGTTGGCACAACTATTTACAATGCGGCCAAGTT
  61 ---------+---------+---------+---------+---------+---------+ 120
        CTTTCGTGCACATTTTACAAAGGGCGCGCAACCGTGTTGATAAATGTTACGCCGGTTCAA
```

Fig. 1 B

```
       ATAAAAGATTCTAATCTGATATGTTTTAAAACACCTTTGCGGCCCGAGTTGTTTGCGTAC
121    ---------+---------+---------+---------+---------+---------+ 180
       TATTTTCTAAGATTAGACTATACAAAATTTTGTGGAAACGCCGGGCTCAACAAACGCATG

GTGACTAGCGAAGAAGATGTGTGGACCGCAGAACAGATAGTAAAACAAAACCCTAGTATT
181    ---------+---------+---------+---------+---------+---------+ 240
       CACTGATCGCTTCTTCTACACACCTGGCGTCTTGTCTATCATTTTGTTTTGGGATCATAA

GGAGCAATAATCGATTTAACCAACACGTCTAAATATTATGATGGTGTGCATTTTTTGCGG
241    ---------+---------+---------+---------+---------+---------+ 300
       CCTCGTTATTAGCTAAATTGGTTGTGCAGATTTATAATACTACCACACGTAAAAAACGCC

GCGGGCCTGTTATACAAAAAAATTCAAGTACCTGGCCAGACTTTGCCGCCTGAAAGCATA
301    ---------+---------+---------+---------+---------+---------+ 360
       CGCCCGGACAATATGTTTTTTTAAGTTCATGGACCGGTCTGAAACGGCGGACTTTCGTAT

GTTCAAGAATTTATTGACACGGTAAAAGAATTTACAGAAAAGTGTCCCGGCATGTTGGTG
361    ---------+---------+---------+---------+---------+---------+ 420
       CAAGTTCTTAAATAACTGTGCCATTTTCTTAAATGTCTTTTCACAGGGCCGTACAACCAC

GGCGTGCACTGCACACACGGTATTAATCGCACCGGTTACATGGTGTGCAGATATTTAATG
421    ---------+---------+---------+---------+---------+---------+ 480
       CCGCACGTGACGTGTGTGCCATAATTAGCGTGGCCAATGTACCACACGTCTATAAATTAC

CACACCCTGGGTATTGCGCCGCAGGAAGCCATAGATAGATTCGAAAAGCCAGAGGTCAC
481    ---------+---------+---------+---------+---------+---------+ 540
       GTGTGGGACCCATAACGCGGCGTCCTTCGGTATCTATCTAAGCTTTTTCGGTCTCCAGTG

AAAATTGAAAGACAAAATTACGTTCAAGATTTATTAATTTAATTAATATTATTTGCATTC
541    ---------+---------+---------+---------+---------+---------+ 600
       TTTTAACTTTCTGTTTTAATGCAAGTTCTAAATAATTAAATTAATTATAATAAACGTAAG

TTTAACAAATACTTTATCCTATTTTCAAATTGTTGCGCTTCTTCCAGCGAACCAAAACTA
601    ---------+---------+---------+---------+---------+---------+ 660
       AAATTGTTTATGAAATAGGATAAAAGTTTAACAACGCGAAGAAGGTCGCTTGGTTTTGAT

TGCTTCGCTTGCTCCGTTTAGCTTGTAGCCGATCAGTGGCGTTGTTCCAATCGACGGTAG
```

Fig. 1 C

```
                 ACGAAGCGAACGAGGCAAATCGAACATCGGCTAGTCACCGCAACAAGGTTAGCTGCCATC
   661 ---------+---------+---------+---------+---------+---------+ 720
                 GATTAGGCCGGATATTCTCCACCACAATGTTGGCAACGTTGATGTTACGTTTATGCTTTT

CTAATCCGGCCTATAAGAGGTGGTGTTACAACCGTTGCAACTACAATGCAAATACGAAAA
   721 ---------+---------+---------+---------+---------+---------+ 780
                 GGTTTTCCACGTACGTCTTTTGGCCGGTAATAGCCGTAAACGTAGTGCCGTCGCGCGTCA

CCAAAAGGTGCATGCAGAAAACCGGCCATTATCGGCATTTGCATCACGGCAGCGCGCAGT
   781 ---------+---------+---------+---------+---------+---------+ 840
                 CGCACAACACCGGATGTTTGCGCTTGTCCGCGGGGTATTGAACCGCGCGATCCGACAAAT

GCGTGTTGTGGCCTACAAACGCGAACAGGCGCCCCATAACTTGGCGCGCTAGGCTGTTTA
   841 ---------+---------+---------+---------+---------+---------+ 900
                 CCACCACTTTGGCAACTAAATCGGTGACCTGCGCGTCTTTTTTCTGCATTATTTCGTCTT

901 ---------+---------+---------+---------+---------+---------+ 960
                 GGTGGTGAAACCGTTGATTTAGCCACTGGACGCGCAGAAAAAAGACGTAATAAAGCAGAA

TCTTTTGCATGGTTTCCTGGAAGCCGGTGTACATGCGGTTTAGATCAGTCATGACGCGCG
   961 ---------+---------+---------+---------+---------+---------+ 1020
                 AGAAAACGTACCAAAGGACCTTCGGCCACATGTACGCCAAATCTAGTCAGTACTGCGCGC

TGACCTGCAAATCTTTGGCCTCGATCTGCTTGTCCTTGATGGCAACGATGCGTTCAATAA
  1021 ---------+---------+---------+---------+---------+---------+ 1080
                 ACTGGACGTTTAGAAACCGGAGCTAGACGAACAGGAACTACCGTTGCTACGCAAGTTATT

ACTCTTGTTTTTTAACAAGTTCCTCGGTTTTTTGCGCCACCACCGCTTGCAGCGCGTTTG
  1081 ---------+---------+---------+---------+---------+---------+ 1140
                 TGAGAACAAAAAATTGTTCAAGGAGCCAAAAAACGCGGTGGTGGCGAACGTCGCGCAAAC

TGTGCTCGGTGAATGTCGCAATCAGCTTAGTCACCAACTGTTTGCTCTCCTCCTCCCGTT
  1141 ---------+---------+---------+---------+---------+---------+ 1200
                 ACACGAGCCACTTACAGCGTTAGTCGAATCAGTGGTTGACAAACGAGAGGAGGAGGGCAA

GTTTGATCGCGGGATCGTACTTGCCGGTGCAGAGCACTTGAGGAATTACTTCTTCTAAAA
  1201 ---------+---------+---------+---------+---------+---------+ 1260
```

Fig. 1 D

```
        CAAACTAGCGCCCTAGCATGAACGGCCACGTCTCGTGAACTCCTTAATGAAGAAGATTTT

GCCATTCTTGTAATTCTATGGCGTAAGGCAATTTGGACTTCATAATCAGCTGAATCACGC
1261    ---------+---------+---------+---------+---------+---------+ 1320
        CGGTAAGAACATTAAGATACCGCATTCCGTTAAACCTGAAGTATTAGTCGACTTAGTGCG

CGGATTTAGTAATGAGCACTGTATGCGGCTGCAAATACAGCGGGTCGCCCCTTTTCACGA
1321    ---------+---------+---------+---------+---------+---------+ 1380
        GCCTAAATCATTACTCGTGACATACGCCGACGTTTATGTCGCCCAGCGGGGAAAAGTGCT

CGCTGTTAGAGGTAGGGCCCCCATTTTGGATGGTCTGCTCAAATAACGATTTGTATTTAT
1381    ---------+---------+---------+---------+---------+---------+ 1440
        GCGACAATCTCCATCCCGGGGGTAAAACCTACCAGACGAGTTTATTGCTAAACATAAATA

TGTCTACATGAACACGTATAGCTTTATCACAAACTGTATATTTTAAACTGTTAGCGACGT
1441    ---------+---------+---------+---------+---------+---------+ 1500
        ACAGATGTACTTGTGCATATCGAAATAGTGTTTGACATATAAAATTTGACAATCGCTGCA

CCTTGGCCACGAACCGGACCTGTTGGTCGCGCTCTAGCACGTACCGCAGGTTGAACGTAT
1501    ---------+---------+---------+---------+---------+---------+ 1560
        GGAACCGGTGCTTGGCCTGGACAACCAGCGCGAGATCGTGCATGGCGTCCAACTTGCATA

CTTCTCCAAATTTAAATTCTCCAATTTTAACGCGAGCCATTTTGATACACGTGTGTCGAT
1561    ---------+---------+---------+---------+---------+---------+ 1620
        GAAGAGGTTTAAATTTAAGAGGTTAAAATTGCGCTCGGTAAAACTATGTGCACACAGCTA

TTTGCAACAACTATTGTTTTTTAACGCAAACTAAACTTATTGTGGTAAGCAATAATTAAA
1621    ---------+---------+---------+---------+---------+---------+ 1680
        AAACGTTGTTGATAACAAAAAATTGCGTTTGATTTGAATAACACCATTCGTTATTAATTT

TATGGGGGAACATGCGCCGCTACAACACTCGTCGTTATGAACGCAGACGGCGCCGGTCTC
1681    ---------+---------+---------+---------+---------+---------+ 1740
        ATACCCCCTTGTACGCGGCGATGTTGTGAGCAGCAATACTTGCGTCTGCCGCGGCCAGAG

GGCGCAAGCGGCTAAAACGTGTTGCGCGTTCAACGCGGCAAACATCGCAAAAGCCAATAG
1741    ---------+---------+---------+---------+---------+---------+ 1800
        CCGCGTTCGCCGATTTTGCACAACGCGCAAGTTGCGCCGTTTGTAGCGTTTTCGGTTATC
```

Fig. 1 E

```
      TACAGTTTTGATTTGCATATTAACGGCGATTTTTTAAATTATCTTATTTAATAAATAGTT
1801  ---------+---------+---------+---------+---------+---------+  1860
      ATGTCAAAACTAAACGTATAATTGCCGCTAAAAAATTTAATAGAATAAATTATTTATCAA

ATGACGCCTACAACTCCCCGCCCGCGTTGACTCGCTGCACCTCGAGCAGTTCGTTGACGC
1861  ---------+---------+---------+---------+---------+---------+  1920
      TACTGCGGATGTTGAGGGGCGGGCGCAACTGAGCGACGTGGAGCTCGTCAAGCAACTGCG

CTTCCTCCGTGTGGCCGAACACGTCGAGCGGGTGGTCGATGACCAGCGGCGTGCCGCACG
1921  ---------+---------+---------+---------+---------+---------+  1980
      GAAGGAGGCACACCGGCTTGTGCAGCTCGCCCACCAGCTACTGGTCGCCGCACGGCGTGC

CGACGCACAAGTATCTGTACACCGAATGATCGTCGGGCGAAGGCACGTCGGCCTCCAAGT
1981  ---------+---------+---------+---------+---------+---------+  2040
      GCTGCGTGTTCATAGACATGTGGCTTACTAGCAGCCCGCTTCCGTGCAGCCGGAGGTTCA

GGCAATATTGGCAAATTCGAAAATATATACAGTTGGGTTGTTTGCGCATATCTATCGTGG
2041  ---------+---------+---------+---------+---------+---------+  2100
      CCGTTATAACCGTTTAAGCTTTTATATATGTCAACCCAACAAACGCGTATAGATAGCACC

CGTTGGGCATGTACGTCCGAACGTTGATTTGCATGCAAGCCGAAATTAAATCATTGCGAT
2101  ---------+---------+---------+---------+---------+---------+  2160
      GCAACCCGTACATGCAGGCTTGCAACTAAACGTACGTTCGGCTTTAATTTAGTAACGCTA

TAGTGCGATTAAAACGTTGTACATCCTCGCTTTTAATCATGCCGTCGATTAAATCGCGCA
2161  ---------+---------+---------+---------+---------+---------+  2220
      ATCACGCTAATTTTGCAACATGTAGGAGCGAAAATTAGTACGGCAGCTAATTTAGCGCGT

ATCGAGTCAAGTGATCAAAGTGTGGAATAATGTTTTCTTTGTATTCCCGAGTCAAGCGCA
2221  ---------+---------+---------+---------+---------+---------+  2280
      TAGCTCAGTTCACTAGTTTCACACCTTATTACAAAAGAAACATAAGGGCTCAGTTCGCGT

GCGCGTATTTTAACAAACTAGCCATCTTGTAAGTTAGTTTCATTTAATGCAACTTTATCC
2281  ---------+---------+---------+---------+---------+---------+  2340
      CGCGCATAAAATTGTTTGATCGGTAGAACATTCAATCAAAGTAAATTACGTTGAAATAGG

AATAATATATTATGTATCGCACGTCAAGAATTAACAATGCGCCCGTTGTCGCATCTCAAC
```

Fig. 1 F

```
2341 ---------+---------+---------+---------+---------+---------+ 2400
     TTATTATATAATACATAGCGTGCAGTTCTTAATTGTTACGCGGGCAACAGCGTAGAGTTG

ACGACTATGATAGAGATCAAATAAAGCGCGAATTAAATAGCTTGCGACGCAACGTGCACG
2401 ---------+---------+---------+---------+---------+---------+ 2460
     TGCTGATACTATCTCTAGTTTATTTCGCGCTTAATTTATCGAACGCTGCGTTGCACGTGC

ATCTGTGCACGCGTTCCGGCACGAGCTTTGATTGTAATAAGTTTTTACGAAGCGATGACA
2461 ---------+---------+---------+---------+---------+---------+ 2520
     TAGACACGTGCGCAAGGCCGTGCTCGAAACTAACATTATTCAAAAATGCTTCGCTACTGT

TGACCCCCGTAGTGACAACGATCACGCCCAAAAGAACTGCCGACTACAAAATTACCGAGT
2521 ---------+---------+---------+---------+---------+---------+ 2580
     ACTGGGGGCATCACTGTTGCTAGTGCGGGTTTTCTTGACGGCTGATGTTTTAATGGCTCA

ATGTCGGTGACGTTAAAACTATTAAGCCATCCAATCGACCGTTAGTCGAATCAGGACCGC
2581 ---------+---------+---------+---------+---------+---------+ 2640
     TACAGCCACTGCAATTTTGATAATTCGGTAGGTTAGCTGGCAATCAGCTTAGTCCTGGCG

TGGTGCGAGAAGCCGCGAAGTATGGCGAATGCATCGTATAACGTGTGGAGTCCGCTCATT
2641 ---------+---------+---------+---------+---------+---------+ 2700
     ACCACGCTCTTCGGCGCTTCATACCGCTTACGTAGCATATTGCACACCTCAGGCGAGTAA

AGAGCGTCATGTTTAGACAAGAAAGCTACATATTTAATTGATCCCGATGATTTTATTGAT
2701 ---------+---------+---------+---------+---------+---------+ 2760
     TCTCGCAGTACAAATCTGTTCTTTCGATGTATAAATTAACTAGGGCTACTAAAATAACTA

AAATTGACCCTAACTCCATACACGGTATTCTACAATGGCGGGGTTTTGGTCAAAATTTCC
2761 ---------+---------+---------+---------+---------+---------+ 2820
     TTTAACTGGGATTGAGGTATGTGCCATAAGATGTTACCGCCCCAAAACCAGTTTTAAAGG

GGACTGCGATTGTACATGCTGTTAACGGCTCCGCCCACTATTAATGAAATTAAAAATTCC
2821 ---------+---------+---------+---------+---------+---------+ 2880
     CCTGACGCTAACATGTACGACAATTGCCCGAGGCGGGTGATAATTACTTTAATTTTTAAGG

AATTTTAAAAAACGCAGCAAGAGAAACATTTGTATGAAAGAATGCGTAGAAGGAAAGAAA
2881 ---------+---------+---------+---------+---------+---------+ 2940
```

Fig. 1 G

```
        TTAAAATTTTTTGCGTCGTTCTCTTTGTAAACATACTTTCTTACGCATCTTCCTTTCTTT

AATGTCGTCGACATGCTGAACAACAAGATTAATATGCCTCCGTGTATAAAAAAATATTG
2941 ---------+---------+---------+---------+---------+---------+ 3000
        TTACAGCAGCTGTACGACTTGTTGTTCTAATTATACGGAGGCACATATTTTTTTATAAC

AACGATTTGAAAGAAAACAATGTACCGCGCGGCGGTATGTACAGGAAGAGGTTTATACTA
3001 ---------+---------+---------+---------+---------+---------+ 3060
        TTGCTAAACTTTCTTTTGTTACATGGCGCGCCGCCATACATGTCCTTCTCCAAATATGAT

AACTGTTACATTGCAAACGTGGTTTCGTGTGCCAAGTGTGAAAACCGATGTTTAATCAAG
3061 ---------+---------+---------+---------+---------+---------+ 3120
        TTGACAATGTAACGTTTGCACCAAAGCACACGGTTCACACTTTTGGCTACAAATTAGTTC

GCTCTGACGCATTTCTACAACCACGACTCCAAGTGTGTGGGTGAAGTCATGCATCTTTTA
3121 ---------+---------+---------+---------+---------+---------+ 3180
        CGAGACTGCGTAAAGATGTTGGTGCTGAGGTTCACACACCCACTTCAGTACGTAGAAAAT

ATCAAATCCCAAGATGTGTATAAACCACCAAACTGCCAAAAAATGAAAACTGTCGACAAG
3181 ---------+---------+---------+---------+---------+---------+ 3240
        TAGTTTAGGGTTCTACACATATTTGGTGGTTTGACGGTTTTTTACTTTTGACAGCTGTTC

CTCTGTCCGTTTGCTGGCAACTGCAAGGGTCTCAATCCTATTTGTAATTATTGAATAATA
3241 ---------+---------+---------+---------+---------+---------+ 3300
        GAGACAGGCAAACGACCGTTGACGTTCCCAGAGTTAGGATAAACATTAATAACTTATTAT

AAACAATTATAAATGCTAAATTTGTTTTTTATTAACGATACAAACCAAACGCAACAAGAA
3301 ---------+---------+---------+---------+---------+---------+ 3360
        TTTGTTAATATTTACGATTTAAACAAAAAATAATTGCTATGTTTGGTTTGCGTTGTTCTT

CATTTGTAGTATTATCTATAATTGAAAACGCGTAGTTATAATCGCTGAGGTAATATTTAA
3361 ---------+---------+---------+---------+---------+---------+ 3420
        GTAAACATCATAATAGATATTAACTTTTGCGCATCAATATTAGCGACTCCATTATAAATT

AATCATTTTCAAATGATTCACAGTTAATTTGCGACAATATAATTTTATTTTCACATAAAC
3421 ---------+---------+---------+---------+---------+---------+ 3480
        TTAGTAAAAGTTTACTAAGTGTCAATTAAACGCTGTTATATTAAAATAAAAGTGTATTTG
```

Fig. 1 H

```
        TAGACGCCTTGTCGTCTTCTTCTTCGTATTCCTTCTCTTTTTCATTTTTCTCCTCATAAA
3481    ---------+---------+---------+---------+---------+---------+  3540
        ATCTGCGGAACAGCAGAAGAAGAAGCATAAGGAAGAGAAAAAGTAAAAAGAGGAGTATTT

AATTAACATAGTTATTATCGTATCCATATATGTATCTATCGTATAGAGTAAATTTTTTGT
3541    ---------+---------+---------+---------+---------+---------+  3600
        TTAATTGTATCAATAATAGCATAGGTATATACATAGATAGCATATCTCATTTAAAAAACA

TGTCATAAATATATATGTCTTTTTTAATGGGGTGTATAGTACCGCTGCGCATAGTTTTTC
3601    ---------+---------+---------+---------+---------+---------+  3660
        ACAGTATTTATATATACAGAAAAAATTACCCCACATATCATGGCGACGCGTATCAAAAAG

TGTAATTTACAACAGTGCTATTTTCTGGTAGTTCTTCGGAGTGTGTTGCTTTAATTATTA
3661    ---------+---------+---------+---------+---------+---------+  3720
        ACATTAAATGTTGTCACGATAAAAGACCATCAAGAAGCCTCACACAACGAAATTAATAAT

AATTTATATAATCAATGAATTTGGGATCGTCGGTTTTGTACAATATGTTGCCGGCATAGT
3721    ---------+---------+---------+---------+---------+---------+  3780
        TTAAATATATTAGTTACTTAAACCCTAGCAGCCAAAACATGTTATACAACGGCCGTATCA

ACGCAGCTTCTTCTAGTTCAATTACACCATTTTTTAGCAGCACCGGATTAACATAACTTT
3781    ---------+---------+---------+---------+---------+---------+  3840
        TGCGTCGAAGAAGATCAAGTTAATGTGGTAAAAAATCGTCGTGGCCTAATTGTATTGAAA

CCAAAATGTTGTACGAACCGTTAAACAAAAACAGTTCACCTCCCTTTTCTATACTATTGT
3841    ---------+---------+---------+---------+---------+---------+  3900
        GGTTTTACAACATGCTTGGCAATTTGTTTTTGTCAAGTGGAGGGAAAAGATATGATAACA

CTGCGAGCAGTTGTTTGTTGTTAAAAATAACAGCCATTGTAATGAGACGCACAAACTAAT
3901    ---------+---------+---------+---------+---------+---------+  3960
        GACGCTCGTCAACAAACAACAATTTTATTGTCGGTAACATTACTCTGCGTGTTTGATTA

ATCACAAACTGGAAATGTCTATCAATATATAGTTGCTGATATCATGGAGATAATTAAAAT
3961    ---------+---------+---------+---------+---------+---------+  4020
        TAGTGTTTGACCTTTACAGATAGTTATATATCAACGACTATAGTACCTCTATTAATTTTA

GATAACCATCTCGCAAATAAATAAGTATTTTACTGTTTTCGTAACAGTTTTGTAATAAAA
```

Fig. 1 I

```
4021 ---------+---------+---------+---------+---------+---------+ 4080
     CTATTGGTAGAGCGTTTATTTATTCATAAAATGACAAAAGCATTGTCAAAACATTATTTT

AAACCTATAAATATTCCGGATTATTCATACCGTCCCACCATCGGGCGCGGATCCCGGGTA
4081 ---------+---------+---------+---------+---------+---------+ 4140
     TTTGGATATTTATAAGGCCTAATAAGTATGGCAGGGTGGTAGCCCGCGCCTAGGGCCCAT

XbaI
       |
     CCTTCTAGACACCATGTACAACATGCGGCGATTAAGTCTTTCACCCACCTTTTCAATGGG
4141 ---------+---------+---------+---------+---------+---------+ 4200
     GGAAGATCTGTGGTACATGTTGTACGCCGCTAATTCAGAAAGTGGGTGGAAAAGTTACCC

M  Y  N  M  R  R  L  S  L  S  P  T  F  S  M  G  -

ATTTCATCTGTTAGTTACTGTGAGTCTCTTATTTTCCCATGTGGACCATGTAATTGCTGA
4201 ---------+---------+---------+---------+---------+---------+ 4260
     TAAAGTAGACAATCAATGACACTCAGAGAATAAAAGGGTACACCTGGTACATTAACGACT b     F  H  L  L  V  T  V  S  L  L  F  S  H  V  D  H  V  I  A  E  -

GACAGAAATGGAAGGAGAAGGAAATGAAACTGGTGAATGTACTGGATCATATTACTGTAA
4261 ---------+---------+---------+---------+---------+---------+ 4320
     CTGTCTTTACCTTCCTCTTCCTTTACTTTGACCACTTACATGACCTAGTATAATGACATT b     T  E  M  E  G  E  G  N  E  T  G  E  C  T  G  S  Y  Y  C  K  -

GAAAGGGGTGATTTTGCCCATTTGGGAACCCCAAGACCCTTCTTTTGGGGACAAAATTGC
4321 ---------+---------+---------+---------+---------+---------+ 4380
     CTTTCCCCACTAAAACGGGTAAACCCTTGGGGTTCTGGGAAGAAAACCCCTGTTTTAACG b     K  G  V  I  L  P  I  W  E  P  Q  D  P  S  F  G  D  K  I  A  -

TAGAGCTACTGTGTATTTTGTGGCCATGGTCTACATGTTTCTTGGAGTCTCTATCATAGC
4381 ---------+---------+---------+---------+---------+---------+ 4440
     ATCTCGATGACACATAAAACACCGGTACCAGATGTACAAAGAACCTCAGAGATAGTATCG
```

TGATCGGTTCATGTCCTCTATAGAAGTCATCACATCTCAAGAAAAAGAAATAACCATAAA
     4441  ---------+---------+---------+---------+---------+---------+  4500
           ACTAGCCAAGTACAGGAGATATCTTCAGTAGTGTAGAGTTCTTTTTCTTTATTGGTATTT b          D   R   F   M   S   S   I   E   V   I   T   S   Q   E   K   E   I   T   I   K   -

GAAACCCAATGGAGAGACCACCAAGACAACTGTGAGGATCTGGAATGAAACAGTTTCTAA
     4501  ---------+---------+---------+---------+---------+---------+  4560
           CTTTGGGTTACCTCTCTGGTGGTTCTGTTGACACTCCTAGACCTTACTTTGTCAAAGATT b          K   P   N   G   E   T   T   K   T   T   V   R   I   W   N   E   T   V   S   N   -

CCTGACCTTGATGGCCCTGGGATCTTCTGCTCCTGAGATTCTCCTTTCAGTAATTGAAGT
     4561  ---------+---------+---------+---------+---------+---------+  4620
           GGACTGGAACTACCGGGACCCTAGAAGACGAGGACTCTAAGAGGAAAGTCATTAACTTCA b          L   T   L   M   A   L   G   S   S   A   P   E   I   L   L   S   V   I   E   V   -

GTGTGGCCATAACTTCACTGCAGGAGACCTCGGTCCTAGCACCATCGTGGGAAGTGCTGC
     4621  ---------+---------+---------+---------+---------+---------+  4680
           CACACCGGTATTGAAGTGACGTCCTCTGGAGCCAGGATCGTGGTAGCACCCTTCACGACG b          C   G   H   N   F   T   A   G   D   L   G   P   S   T   I   V   G   S   A   A   -

ATTCAATATGTTCATCATTATTGCACTCTGTGTTTATGTGGTGCCTGACGGAGAGACAAG
     4681  ---------+---------+---------+---------+---------+---------+  4740
           TAAGTTATACAAGTAGTAATAACGTGAGACACAAATACACCACGGACTGCCTCTCTGTTC b          F   N   M   F   I   I   I   A   L   C   V   Y   V   V   P   D   G   E   T   R   -

GAAGATTAAGCATTTGCGTGTCTTCTTTGTGACAGCAGCCTGGAGCATCTTTGCCTACAC
     4741  ---------+---------+---------+---------+---------+---------+  4800
           CTTCTAATTCGTAAACGCACAGAAGAAACACTGTCGTCGGACCTCGTAGAAACGGATGTG b          K   I   K   H   L   R   V   F   F   V   T   A   A   W   S   I   F   A   Y   T   -
```

Fig. 1 K

```
            CTGGCTTTACATTATTTTGTCTGTCATATCTCCTGGTGTTGTGGAGGTCTGGGAAGGTTT
       4801 ---------+---------+---------+---------+---------+---------+ 4860
            GACCGAAATGTAATAAAACAGACAGTATAGAGGACCACAACACCTCCAGACCCTTCCAAA b           W  L  Y  I  I  L  S  V  I  S  P  G  V  V  E  V  W  E  G  L  -

GCTTACTTTCTTCTTCTTTCCCATCTGTGTTGTGTTCGCTTGGGTAGCGGATAGGAGACT
       4861 ---------+---------+---------+---------+---------+---------+ 4920
            CGAATGAAAGAAGAAGAAAGGGTAGACACAACACAAGCGAACCCATCGCCTATCCTCTGA b           L  T  F  F  F  F  P  I  C  V  V  F  A  W  V  A  D  R  R  L  -

TCTGTTTTACAAGTATGTCTACAAGAGGTATCGAGCTGGCAAGCAGAGGGGGATGATTAT
       4921 ---------+---------+---------+---------+---------+---------+ 4980
            AGACAAAATGTTCATACAGATGTTCTCCATAGCTCGACCGTTCGTCTCCCCCTACTAATA b           L  F  Y  K  Y  V  Y  K  R  Y  R  A  G  K  Q  R  G  M  I  I  -

TGAACATGAAGGAGACAGGCCATCTTCTAAGACTGAAATTGAAATGGACGGGAAAGTGGT
       4981 ---------+---------+---------+---------+---------+---------+ 5040
            ACTTGTACTTCCTCTGTCCGGTAGAAGATTCTGACTTTAACTTTACCTGCCCTTTCACCA b           E  H  E  G  D  R  P  S  S  K  T  E  I  E  M  D  G  K  V  V  -

CAATTCTCATGTTGAAAATTTCTTAGATGGTGCTCTGGTTCTGGAGGTGGATGAGAGGGA
       5041 ---------+---------+---------+---------+---------+---------+ 5100
            GTTAAGAGTACAACTTTTAAAGAATCTACCACGAGACCAAGACCTCCACCTACTCTCCCT b           N  S  H  V  E  N  F  L  D  G  A  L  V  L  E  V  D  E  R  D  -

CCAAGATGATGAAGAAGCTAGGCGAGAAATGGCTAGGATTCTGAAGGAACTTAAGCAGAA
       5101 ---------+---------+---------+---------+---------+---------+ 5160
            GGTTCTACTACTTCTTCGATCCGCTCTTTACCGATCCTAAGACTTCCTTGAATTCGTCTT b           Q  D  D  E  E  A  R  R  E  M  A  R  I  L  K  E  L  K  Q  K  -

GCATCCAGATAAAGAAATAGAGCAATTAATAGAATTAGCTAACTACCAAGTCCTAAGTCA
```

Fig. 1 L

```
                    5161 ---------+---------+---------+---------+---------+---------+ 5220
                         CGTAGGTCTATTTCTTTATCTCGTTAATTATCTTAATCGATTGATGGTTCAGGATTCAGT b        H   P   D   K   E   I   E   Q   L   I   E   L   A   N   Y   Q   V   L   S   Q   -

GCAGCAAAAAAGTAGAGCATTTTATCGCATTCAAGCTACTCGCCTCATGACTGGAGCTGG
                    5221 ---------+---------+---------+---------+---------+---------+ 5280
                         CGTCGTTTTTTCATCTCGTAAAATAGCGTAAGTTCGATGAGCGGAGTACTGACCTCGACC b        Q   Q   K   S   R   A   F   Y   R   I   Q   A   T   R   L   M   T   G   A   G   -

CAACATTTTAAAGAGGCATGCAGCTGACCAAGCAAGGAAGGCTGTCAGCATGCACGAGGT
                    5281 ---------+---------+---------+---------+---------+---------+ 5340
                         GTTGTAAAATTTCTCCGTACGTCGACTGGTTCGTTCCTTCCGACAGTCGTACGTGCTCCA b        N   I   L   K   R   H   A   A   D   Q   A   R   K   A   V   S   M   H   E   V   -

CAACACTGAAGTGACTGAAAATGACCCTGTTAGTAAGATCTTCTTTGAACAAGGGACATA
                    5341 ---------+---------+---------+---------+---------+---------+ 5400
                         GTTGTGACTTCACTGACTTTTACTGGGACAATCATTCTAGAAGAAACTTGTTCCCTGTAT b        N   T   E   V   T   E   N   D   P   V   S   K   I   F   F   E   Q   G   T   Y   -

TCAGTGTCTGGAGAACTGTGGTACTGTGGCCCTTACCATTATCCGCAGAGGTGGTGATTT
                    5401 ---------+---------+---------+---------+---------+---------+ 5460
                         AGTCACAGACCTCTTGACACCATGACACCGGGAATGGTAATAGGCGTCTCCACCACTAAA b        Q   C   L   E   N   C   G   T   V   A   L   T   I   I   R   R   G   G   D   L   -

GACTAACACTGTGTTTGTTGACTTCAGAACAGAGGATGGCACAGCAAATGCTGGGTCTGA
                    5461 ---------+---------+---------+---------+---------+---------+ 5520
                         CTGATTGTGACACAAACAACTGAAGTCTTGTCTCCTACCGTGTCGTTTACGACCCAGACT b        T   N   T   V   F   V   D   F   R   T   E   D   G   T   A   N   A   G   S   D   -

TTATGAATTTACTGAAGGAACTGTGGTGTTTAAGCCTGGTGATACCCAGAAGGAAATCAG
                    5521 ---------+---------+---------+---------+---------+---------+ 5580
```

Fig. 1 M

```
            AATACTTAAATGACTTCCTTGACACCACAAATTCGGACCACTATGGGTCTTCCTTTAGTC b        Y  E  F  T  E  G  T  V  V  F  K  P  G  D  T  Q  K  E  I  R   -

AGTGGGTATCATAGATGATGATATCTTTGAGGAGGATGAAAATTTCCTTGTGCATCTCAG
    5581 ---------+---------+---------+---------+---------+---------+ 5640
         TCACCCATAGTATCTACTACTATAGAAACTCCTCCTACTTTTAAAGGAACACGTAGAGTC b        V  G  I  I  D  D  D  I  F  E  E  D  E  N  F  L  V  H  L  S   -

CAATGTCAAAGTATCTTCTGAAGCTTCAGAAGATGGCATACTGGAAGCCAATCATGTTTC
    5641 ---------+---------+---------+---------+---------+---------+ 5700
         GTTACAGTTTCATAGAAGACTTCGAAGTCTTCTACCGTATGACCTTCGGTTAGTACAAAG b        N  V  K  V  S  S  E  A  S  E  D  G  I  L  E  A  N  H  V  S   -

TACACTTGCTTGCCTCGGATCTCCCTCCACTGCCACTGTAACTATTTTTGATGATGACCA
    5701 ---------+---------+---------+---------+---------+---------+ 5760
         ATGTGAACGAACGGAGCCTAGAGGGAGGTGACGGTGACATTGATAAAAACTACTACTGGT b        T  L  A  C  L  G  S  P  S  T  A  T  V  T  I  F  D  D  D  H   -

CGCAGGCATTTTTACTTTTGAGGAACCTGTGACTCATGTGAGTGAGAGCATTGGCATCAT
    5761 ---------+---------+---------+---------+---------+---------+ 5820
         GCGTCCGTAAAAATGAAAACTCCTTGGACACTGAGTACACTCACTCTCGTAACCGTAGTA b        A  G  I  F  T  F  E  E  P  V  T  H  V  S  E  S  I  G  I  M   -

GGAGGTGAAAGTATTGAGAACATCTGGAGCTCGAGGAAATGTTATCGTTCCATATAAAAC
    5821 ---------+---------+---------+---------+---------+---------+ 5880
         CCTCCACTTTCATAACTCTTGTAGACCTCGAGCTCCTTTACAATAGCAAGGTATATTTTG b        E  V  K  V  L  R  T  S  G  A  R  G  N  V  I  V  P  Y  K  T   -

CATCGAAGGGACTGCCAGAGGTGGAGGGGAGGATTTTGAGGACACTTGTGGAGAGCTCGA
    5881 ---------+---------+---------+---------+---------+---------+ 5940
         GTAGCTTCCCTGACGGTCTCCACCTCCCCTCCTAAAACTCCTGTGAACACCTCTCGAGCT
```

ATTCCAGAATGATGAAATTGTCAAAACAATATCAGTCAAGGTAATTGATGATGAGGAGTA
    5941 ---------+---------+---------+---------+---------+---------+ 6000
         TAAGGTCTTACTACTTTAACAGTTTTGTTATAGTCAGTTCCATTAACTACTACTCCTCAT b        F  Q  N  D  E  I  V  K  T  I  S  V  K  V  I  D  D  E  E  Y  -

TGAGAAAAACAAGACCTTCTTCCTTGAGATTGGAGAGCCCCGCCTGGTGGAGATGAGTGA
    6001 ---------+---------+---------+---------+---------+---------+ 6060
         ACTCTTTTTGTTCTGGAAGAAGGAACTCTAACCTCTCGGGGCGGACCACCTCTACTCACT b        E  K  N  K  T  F  F  L  E  I  G  E  P  R  L  V  E  M  S  E  -

GAAGAAAGCCCTGTTATTGAATGAGCTTGGTGGCTTCACAATAACAGGAAAATACCTGTT
    6061 ---------+---------+---------+---------+---------+---------+ 6120
         CTTCTTTCGGGACAATAACTTACTCGAACCACCGAAGTGTTATTGTCCTTTTATGGACAA b        K  K  A  L  L  N  E  L  G  G  F  T  I  T  G  K  Y  L  F  -

TGGCCAACCTGTCTTCAGGAAGGTTCATGCTAGAGAACATCCGATTCTCTCTACTGTAAT
    6121 ---------+---------+---------+---------+---------+---------+ 6180
         ACCGGTTGGACAGAAGTCCTTCCAAGTACGATCTCTTGTAGGCTAAGAGAGATGACATTA b        G  Q  P  V  F  R  K  V  H  A  R  E  H  P  I  L  S  T  V  I  -

CACCATTGCAGACGAATATGATGACAAGCAGCCACTGACCAGCAAAGAGGAAGAGGAGAG
    6181 ---------+---------+---------+---------+---------+---------+ 6240
         GTGGTAACGTCTGCTTATACTACTGTTCGTCGGTGACTGGTCGTTTCTCCTTCTCCTCTC b        T  I  A  D  E  Y  D  D  K  Q  P  L  T  S  K  E  E  E  E  R  -

GCGCATTGCAGAAATGGGGCGCCCCATCCTGGGAGAGCACACCAAGTTGGAAGTGATCAT
    6241 ---------+---------+---------+---------+---------+---------+ 6300
         CGCGTAACGTCTTTACCCCGCGGGGTAGGACCCTCTCGTGTGGTTCAACCTTCACTAGTA b        R  I  A  E  M  G  R  P  I  L  G  E  H  T  K  L  E  V  I  I  -
```

Fig. 1 O

```
         TGAAGAATCCTATGAATTCAAGAGTACTGTGGACAAACTCATTAAGAAGACAAACCTGGC
   6301  ---------+---------+---------+---------+---------+---------+  6360
         ACTTCTTAGGATACTTAAGTTCTCATGACACCTGTTTGAGTAATTCTTCTGTTTGGACCG b         E  E  S  Y  E  F  K  S  T  V  D  K  L  I  K  K  T  N  L  A   -

CCTTGTGGTTGGGACTAACAGCTGGAGAGAACAGTTCATTGAAGCTATCACTGTCAGTGC
   6361  ---------+---------+---------+---------+---------+---------+  6420
         GGAACACCAACCCTGATTGTCGACCTCTCTTGTCAAGTAACTTCGATAGTGACAGTCACG b         L  V  V  G  T  N  S  W  R  E  Q  F  I  E  A  I  T  V  S  A   -

TGGGGAAGATGATGACGACGATGAATGTGGGGAAGAGAAGCTGCCCTCCTGTTTCGATTA
   6421  ---------+---------+---------+---------+---------+---------+  6480
         ACCCCTTCTACTACTGCTGCTACTTACACCCCTTCTCTTCGACGGGAGGACAAAGCTAAT b         G  E  D  D  D  D  E  C  G  E  E  K  L  P  S  C  F  D  Y   -

CGTGATGCACTTTCTGACTGTGTTCTGGAAGGTCCTGTTTGCCTTCGTCCCCCCTACTGA
   6481  ---------+---------+---------+---------+---------+---------+  6540
         GCACTACGTGAAAGACTGACACAAGACCTTCCAGGACAAACGGAAGCAGGGGGGATGACT b         V  M  H  F  L  T  V  F  W  K  V  L  F  A  F  V  P  P  T  E   -

ATACTGGAATGGCTGGGCGTGTTTCATTGTCTCCATCCTCATGATTGGCCTACTGACAGC
   6541  ---------+---------+---------+---------+---------+---------+  6600
         TATGACCTTACCGACCCGCACAAAGTAACAGAGGTAGGAGTACTAACCGGATGACTGTCG b         Y  W  N  G  W  A  C  F  I  V  S  I  L  M  I  G  L  L  T  A   -

TTTCATTGGAGACCTGGCTTCCCACTTTGGCTGCACCATTGGCCTGAAAGATTCTGTGAC
   6601  ---------+---------+---------+---------+---------+---------+  6660
         AAAGTAACCTCTGGACCGAAGGGTGAAACCGACGTGGTAACCGGACTTTCTAAGACACTG b         F  I  G  D  L  A  S  H  F  G  C  T  I  G  L  K  D  S  V  T   -

TGCAGTCGTGTTCGTCGCACTTGGAACATCAGTGCCAGACACATTTGCCAGCAAAGTGGC
```

Fig. 1 P

```
6661 ---------+---------+---------+---------+---------+---------+ 6720
     ACGTCAGCACAAGCAGCGTGAACCTTGTAGTCACGGTCTGTGTAAACGGTCGTTTCACCG b      A  V  V  F  V  A  L  G  T  S  V  P  D  T  F  A  S  K  V  A  -

AGCCACCCAGGACCAGTATGCAGACGCCTCCATAGGTAACGTCACGGGCAGCAACGCGGT
6721 ---------+---------+---------+---------+---------+---------+ 6780
     TCGGTGGGTCCTGGTCATACGTCTGCGGAGGTATCCATTGCAGTGCCCGTCGTTGCGCCA b      A  T  Q  D  Q  Y  A  D  A  S  I  G  N  V  T  G  S  N  A  V  -

GAATGTCTTCCTGGGAATCGGTGTGGCCTGGTCCATCGCTGCCATCTACCACGCAGCCAA
6781 ---------+---------+---------+---------+---------+---------+ 6840
     CTTACAGAAGGACCCTTAGCCACACCGGACCAGGTAGCGACGGTAGATGGTGCGTCGGTT b      N  V  F  L  G  I  G  V  A  W  S  I  A  A  I  Y  H  A  A  N  -

TGGGGAACAGTTCAAAGTGTCCCCTGGCACACTAGCTTTCTCTGTCACTCTCTTCACCAT
6841 ---------+---------+---------+---------+---------+---------+ 6900
     ACCCCTTGTCAAGTTTCACAGGGGACCGTGTGATCGAAAGAGACAGTGAGAGAAGTGGTA b      G  E  Q  F  K  V  S  P  G  T  L  A  F  S  V  T  L  F  T  I  -

TTTTGCTTTCATCAATGTGGGGGTGCTGCTGTATCGGCGGAGGCCAGAAATCGGAGGTGA
6901 ---------+---------+---------+---------+---------+---------+ 6960
     AAAACGAAAGTAGTTACACCCCCACGACGACATAGCCGCCTCCGGTCTTTAGCCTCCACT b      F  A  F  I  N  V  G  V  L  L  Y  R  R  R  P  E  I  G  G  E  -

GCTGGGTGGGCCCCGGACTGCCAAGCTCCTCACATCCTGCCTCTTTGTGCTCCTATGGCT
6961 ---------+---------+---------+---------+---------+---------+ 7020
     CGACCCACCCGGGGCCTGACGGTTCGAGGAGTGTAGGACGGAGAAACACGAGGATACCGA b      L  G  G  P  R  T  A  K  L  L  T  S  C  L  F  V  L  L  W  L  -
```

Fig. 1 Q

```
        CTTGTACATTTTCTTCTCCTCCCTGGAGGCCTACTGCCACATAAAAGGCTTCTAAGCGGC
  7021  ---------+---------+---------+---------+---------+---------+  7080
        GAACATGTAAAAGAAGAGGAGGGACCTCCGGATGACGGTGTATTTTCCGAAGATTCGCCG b          L  Y  I  F  F  S  S  L  E  A  Y  C  H  I  K  G  F  *

CGCTGCAGATCTGATCCTTTCCTGGGACCCGGCAAGAACCAAAAACTCACTCTCTTCAAG
  7081  ---------+---------+---------+---------+---------+---------+  7140
        GCGACGTCTAGACTAGGAAAGGACCCTGGGCCGTTCTTGGTTTTTGAGTGAGAGAAGTTC

GAAATCCGTAATGTTAAACCCGACACGATGAAGCTTGTCGTTGGATGGAAAGGAAAAGAG
  7141  ---------+---------+---------+---------+---------+---------+  7200
        CTTTAGGCATTACAATTTGGGCTGTGCTACTTCGAACAGCAACCTACCTTTCCTTTTCTC

TTCTACAGGGAAACTTGGACCCGCTTCATGGAAGACAGCTTCCCCATTGTTAACGACCAA
  7201  ---------+---------+---------+---------+---------+---------+  7260
        AAGATGTCCCTTTGAACCTGGGCGAAGTACCTTCTGTCGAAGGGGTAACAATTGCTGGTT

GAAGTGATGGATGTTTTCCTTGTTGTCAACATGCGTCCCACTAGACCCAACCGTTGTTAC
  7261  ---------+---------+---------+---------+---------+---------+  7320
        CTTCACTACCTACAAAAGGAACAACAGTTGTACGCAGGGTGATCTGGGTTGGCAACAATG

AAATTCCTGGCCCAACACGCTCTGCGTTGCGACCCCGACTATGTACCTCATGACGTGATT
  7321  ---------+---------+---------+---------+---------+---------+  7380
        TTTAAGGACCGGGTTGTGCGAGACGCAACGCTGGGGCTGATACATGGAGTACTGCACTAA

AGGATCGTCGAGCCTTCATGGGTGGGCAGCAACAACGAGTACCGCATCAGCCTGGCTAAG
  7381  ---------+---------+---------+---------+---------+---------+  7440
        TCCTAGCAGCTCGGAAGTACCCACCCGTCGTTGTTGCTCATGGCGTAGTCGGACCGATTC

AAGGGCGGCGGCTGCCCAATAATGAACCTTCACTCTGAGTACACCAACTCGTTCGAACAG
  7441  ---------+---------+---------+---------+---------+---------+  7500
        TTCCCGCCGCCGACGGGTTATTACTTGGAAGTGAGACTCATGTGGTTGAGCAAGCTTGTC

TTCATCGATCGTGTCATCTGGGAGAACTTCTACAAGCCCATCGTTTACATCGGTACCGAC
  7501  ---------+---------+---------+---------+---------+---------+  7560
        AAGTAGCTAGCACAGTAGACCCTCTTGAAGATGTTCGGGTAGCAAATGTAGCCATGGCTG
```

Fig. 1 R

```
          TCTGCTGAAGAGGAGGAAATTCTCCTTGAAGTTTCCCTGGTGTTCAAAGTAAAGGAGTTT
    7561  ---------+---------+---------+---------+---------+---------+  7620
          AGACGACTTCTCCTCCTTTAAGAGGAACTTCAAAGGGACCACAAGTTTCATTTCCTCAAA

GCACCAGACGCACCTCTGTTCACTGGTCCGGCGTATTAAAACACGATACATTGTTATTAG
    7621  ---------+---------+---------+---------+---------+---------+  7680
          CGTGGTCTGCGTGGAGACAAGTGACCAGGCCGCATAATTTTGTGCTATGTAACAATAATC

TACATTTATTAAGCGCTAGATTCTGTGCGTTGTTGATTTACAGACAATTGTTGTACGTAT
    7681  ---------+---------+---------+---------+---------+---------+  7740
          ATGTAAATAATTCGCGATCTAAGACACGCAACAACTAAATGTCTGTTAACAACATGCATA

TTTAATAATTCATTAAATTTATAATCTTTAGGGTGGTATGTTAGAGCGAAAATCAAATGA
    7741  ---------+---------+---------+---------+---------+---------+  7800
          AAATTATTAAGTAATTTAAATATTAGAAATCCCACCATACAATCTCGCTTTTAGTTTACT

TTTTCAGCGTCTTTATATCTGAATTTAAATATTAAATCCTCAATAGATTTGTAAAATAGG
    7801  ---------+---------+---------+---------+---------+---------+  7860
          AAAAGTCGCAGAAATATAGACTTAAATTTATAATTTAGGAGTTATCTAAACATTTTATCC

TTTCGATTAGTTTCAAACAAGGGTTGTTTTTCCGAACCGATGGCTGGACTATCTAATGGA
    7861  ---------+---------+---------+---------+---------+---------+  7920
          AAAGCTAATCAAAGTTTGTTCCCAACAAAAAGGCTTGGCTACCGACCTGATAGATTACCT

TTTTCGCTCAACGCCACAAAACTTGCCAAATCTTGTAGCAGCAATCTAGCTTTGTCGATA
    7921  ---------+---------+---------+---------+---------+---------+  7980
          AAAAGCGAGTTGCGGTGTTTTGAACGGTTTAGAACATCGTCGTTAGATCGAAACAGCTAT

TTCGTTTGTGTTTTGTTTTGTAATAAAGGTTCGACGTCGTTCAAAATATTATGCGCTTTT
    7981  ---------+---------+---------+---------+---------+---------+  8040
          AAGCAAACACAAAACAAAACATTATTTCCAAGCTGCAGCAAGTTTTATAATACGCGAAAA

GTATTTCTTTCATCACTGTCGTTAGTGTACAATTGACTCGACGTAAACACGTTAAATAAA
    8041  ---------+---------+---------+---------+---------+---------+  8100
          CATAAAGAAAGTAGTGACAGCAATCACATGTTAACTGAGCTGCATTTGTGCAATTTATTT

GCTTGGACATATTTAACATCGGGCGTGTTAGCTTTATTAGGCCGATTATCGTCGTCGTCC
```

Fig. 1 S

```
8101 ---------+---------+---------+---------+---------+---------+ 8160
     CGAACCTGTATAAATTGTAGCCCGCACAATCGAAATAATCCGGCTAATAGCAGCAGCAGG

CAACCCTCGTCGTTAGAAGTTGCTTCCGAAGACGATTTTGCCATAGCCACACGACGCCTA
8161 ---------+---------+---------+---------+---------+---------+ 8220
     GTTGGGAGCAGCAATCTTCAACGAAGGCTTCTGCTAAAACGGTATCGGTGTGCTGCGGAT

TTAATTGTGTCGGCTAACACGTCCGCGATCAAATTTGTAGTTGAGCTTTTTGGAATTATT
8221 ---------+---------+---------+---------+---------+---------+ 8280
     AATTAACACAGCCGATTGTGCAGGCGCTAGTTTAAACATCAACTCGAAAAACCTTAATAA

TCTGATTGCGGGCGTTTTTGGGCGGGTTTCAATCTAACTGTGCCCGATTTTAATTCAGAC
8281 ---------+---------+---------+---------+---------+---------+ 8340
     AGACTAACGCCCGCAAAAACCCGCCCAAAGTTAGATTGACACGGGCTAAAATTAAGTCTG

AACACGTTAGAAAGCGATGGTGCAGGCGGTGGTAACATTTCAGACGGCAAATCTACTAAT
8341 ---------+---------+---------+---------+---------+---------+ 8400
     TTGTGCAATCTTTCGCTACCACGTCCGCCACCATTGTAAAGTCTGCCGTTTAGATGATTA

GGCGGCGGTGGTGGAGCTGATGATAAATCTACCATCGGTGGAGGCGCAGGCGGGGCTGGC
8401 ---------+---------+---------+---------+---------+---------+ 8460
     CCGCCGCCACCACCTCGACTACTATTTAGATGGTAGCCACCTCCGCGTCCGCCCCGACCG

GGCGGAGGCGGAGGCGGAGGTGGTGGCGGTGATGCAGACGGCGGTTTAGGCTCAAATGTC
8461 ---------+---------+---------+---------+---------+---------+ 8520
     CCGCCTCCGCCTCCGCCTCCACCACCGCCACTACGTCTGCCGCCAAATCCGAGTTTACAG

TCTTTAGGCAACACAGTCGGCACCTCAACTATTGTACTGGTTTCGGGCGCCGTTTTTGGT
8521 ---------+---------+---------+---------+---------+---------+ 8580
     AGAAATCCGTTGTGTCAGCCGTGGAGTTGATAACATGACCAAAGCCCGCGGCAAAAACCA

TTGACCGGTCTGAGACGAGTGCGATTTTTTCGTTTCTAATAGCTTCCAACAATTGTTGT
8581 ---------+---------+---------+---------+---------+---------+ 8640
     AACTGGCCAGACTCTGCTCACGCTAAAAAAAGCAAAGATTATCGAAGGTTGTTAACAACA

CTGTCGTCTAAAGGTGCAGCGGGTTGAGGTTCCGTCGGCATTGGTGGAGCGGGCGGCAAT
8641 ---------+---------+---------+---------+---------+---------+ 8700
     GACAGCAGATTTCCACGTCGCCCAACTCCAAGGCAGCCGTAACCACCTCGCCCGCCGTTA
```

Fig. 1 T

```
      TCAGACATCGATGGTGGTGGTGGTGGTGGAGGCGCTGGAATGTTAGGCACGGGAGAAGGT
8701  ---------+---------+---------+---------+---------+---------+ 8760
      AGTCTGTAGCTACCACCACCACCACCACCTCCGCGACCTTACAATCCGTGCCCTCTTCCA

GGTGGCGGCGGTGCCGCCGGTATAATTTGTTCTGGTTTAGTTTGTTCGCGCACGATTGTG
8761  ---------+---------+---------+---------+---------+---------+ 8820
      CCACCGCCGCCACGGCGGCCATATTAAACAAGACCAAATCAAACAAGCGCGTGCTAACAC

GGCACCGGCGCAGGCGCCGCTGGCTGCACAACGGAAGGTCGTCTGCTTCGAGGCAGCGCT
8821  ---------+---------+---------+---------+---------+---------+ 8880
      CCGTGGCCGCGTCCGCGGCGACCGACGTGTTGCCTTCCAGCAGACGAAGCTCCGTCGCGA

TGGGGTGGTGGCAATTCAATATTATAATTGGAATACAAATCGTAAAAATCTGCTATAAGC
8881  ---------+---------+---------+---------+---------+---------+ 8940
      ACCCCACCACCGTTAAGTTATAATATTAACCTTATGTTTAGCATTTTTAGACGATATTCG

ATTGTAATTTCGCTATCGTTTACCGTGCCGATATTTAACAACCGCTCAATGTAAGCAATT
8941  ---------+---------+---------+---------+---------+---------+ 9000
      TAACATTAAAGCGATAGCAAATGGCACGGCTATAAATTGTTGGCGAGTTACATTCGTTAA

GTATTGTAAAGAGATTGTCTCAAGCTCGCCGCACGCCGATAACAAGCCTTTTCATTTTTA
9001  ---------+---------+---------+---------+---------+---------+ 9060
      CATAACATTTCTCTAACAGAGTTCGAGCGGCGTGCGGCTATTGTTCGGAAAAGTAAAAAT

CTACAGCATTGTAGTGGCGAGACACTTCGCTGTCGTCGACGTACATGTATGCTTTGTTGT
9061  ---------+---------+---------+---------+---------+---------+ 9120
      GATGTCGTAACATCACCGCTCTGTGAAGCGACAGCAGCTGCATGTACATACGAAACAACA

CAAAAACGTCGTTGGCAAGCTTTAAAATATTTAAAAGAACATCTCTGTTCAGCACCACTG
9121  ---------+---------+---------+---------+---------+---------+ 9180
      GTTTTTGCAGCAACCGTTCGAAATTTTATAAATTTTCTTGTAGAGACAAGTCGTGGTGAC

TGTTGTCGTAAATGTTGTTTTTGATAATTTGCGCTTCCGCAGTATCGACACGTTCAAAAA
9181  ---------+---------+---------+---------+---------+---------+ 9240
      ACAACAGCATTTACAACAAAAACTATTAAACGCGAAGGCGTCATAGCTGTGCAAGTTTTT

ATTGATGCGCATCAATTTTGTTGTTCCTATTATTGAATAAATAAGATTGTACAGATTCAT
```

Fig. 1 U

```
9241 ---------+---------+---------+---------+---------+---------+ 9300
     TAACTACGCGTAGTTAAAACAACAAGGATAATAACTTATTTATTCTAACATGTCTAAGTA

ATCTACGATTCGTCATGGCCACCACAAATGCTACGCTGCAAACGCTGGTACAATTTTACG
9301 ---------+---------+---------+---------+---------+---------+ 9360
     TAGATGCTAAGCAGTACCGGTGGTGTTTACGATGCGACGTTTGCGACCATGTTAAAATGC

AAAACTGCAAAAACGTCAAAACTCGGTATAAAATAATCAACGGGCGCTTTGGCAAAATAT
9361 ---------+---------+---------+---------+---------+---------+ 9420
     TTTTGACGTTTTTGCAGTTTTGAGCCATATTTTATTAGTTGCCCGCGAAACCGTTTTATA

CTATTTTATCGCACAAGCCCACTAGCAAATTGTATTTGCAGAAAACAATTTCGGCGCACA
9421 ---------+---------+---------+---------+---------+---------+ 9480
     GATAAAATAGCGTGTTCGGGTGATCGTTTAACATAAACGTCTTTTGTTAAAGCCGCGTGT

ATTTTAACGCTGACGAAATAAAAGTTCACCAGTTAATGAGCGACCACCCAAATTTTATAA
9481 ---------+---------+---------+---------+---------+---------+ 9540
     TAAAATTGCGACTGCTTTATTTTCAAGTGGTCAATTACTCGCTGGTGGGTTTAAAATATT

AAATCTATTTTAATCACGGTTCCATCAACAACCAAGTGATCGTGATGGACTACATTGACT
9541 ---------+---------+---------+---------+---------+---------+ 9600
     TTTAGATAAAATTAGTGCCAAGGTAGTTGTTGGTTCACTAGCACTACCTGATGTAACTGA

GTCCCGATTTATTTGAAACACTACAAATTAAAGGCGAGCTTTCGTACCAACTTGTTAGCA
9601 ---------+---------+---------+---------+---------+---------+ 9660
     CAGGGCTAAATAAACTTTGTGATGTTTAATTTCCGCTCGAAAGCATGGTTGAACAATCGT

ATATTATTAGACAGCTGTGTGAAGCGCTCAACGATTTGCACAAGCACAATTTCATACACA
9661 ---------+---------+---------+---------+---------+---------+ 9720
     TATAATAATCTGTCGACACACTTCGCGAGTTGCTAAACGTGTTCGTGTTAAAGTATGTGT

ACGACATAAAACTCGAAAATGTCTTATATTTCGAAGCACTTGATCGCGTGTATGTTTGCG
9721 ---------+---------+---------+---------+---------+---------+ 9780
     TGCTGTATTTTGAGCTTTTACAGAATATAAAGCTTCGTGAACTAGCGCACATACAAACGC

ATTACGGATTGTGCAAACACGAAAACTCACTTAGCGTGCACGACGGCACGTTGGAGTATT
9781 ---------+---------+---------+---------+---------+---------+ 9840
```

Fig. 1 V

```
        TAATGCCTAACACGTTTGTGCTTTTGAGTGAATCGCACGTGCTGCCGTGCAACCTCATAA

TTAGTCCGGAAAAAATTCGACACACAACTATGCACGTTTCGTTTGACTGGTACGCGGCGT
 9841   ---------+---------+---------+---------+---------+---------+ 9900
        AATCAGGCCTTTTTTAAGCTGTGTGTTGATACGTGCAAAGCAAACTGACCATGCGCCGCA

GTTAACATACAAGTTGCTAACGTAATCATGGTCATAGCTGTTTCCTGTGTGAAATTGTTA
 9901   ---------+---------+---------+---------+---------+---------+ 9960
        CAATTGTATGTTCAACGATTGCATTAGTACCAGTATCGACAAAGGACACACTTTAACAAT

TCCGCTCACAATTCCACACAACATACGAGCCGGAAGCATAAAGTGTAAAGCCTGGGGTGC
 9961   ---------+---------+---------+---------+---------+---------+ 10020
        AGGCGAGTGTTAAGGTGTGTTGTATGCTCGGCCTTCGTATTTCACATTTCGGACCCCACG

CTAATGAGTGAGCTAACTCACATTAATTGCGTTGCGCTCACTGCCCGCTTTCCAGTCGGG
10021   ---------+---------+---------+---------+---------+---------+ 10080
        GATTACTCACTCGATTGAGTGTAATTAACGCAACGCGAGTGACGGGCGAAAGGTCAGCCC

AAACCTGTCGTGCCAGCTGCATTAATGAATCGGCCAACGCGCGGGGAGAGGCGGTTTGCG
10081   ---------+---------+---------+---------+---------+---------+ 10140
        TTTGGACAGCACGGTCGACGTAATTACTTAGCCGGTTGCGCGCCCCTCTCCGCCAAACGC

TATTGGGCGCTCTTCCGCTTCCTCGCTCACTGACTCGCTGCGCTCGGTCGTTCGGCTGCG
10141   ---------+---------+---------+---------+---------+---------+ 10200
        ATAACCCGCGAGAAGGCGAAGGAGCGAGTGACTGAGCGACGCGAGCCAGCAAGCCGACGC

GCGAGCGGTATCAGCTCACTCAAAGGCGGTAATACGGTTATCCACAGAATCAGGGGATAA
10201   ---------+---------+---------+---------+---------+---------+ 10260
        CGCTCGCCATAGTCGAGTGAGTTTCCGCCATTATGCCAATAGGTGTCTTAGTCCCCTATT

CGCAGGAAAGAACATGTGAGCAAAAGGCCAGCAAAAGGCCAGGAACCGTAAAAAGGCCGC
10261   ---------+---------+---------+---------+---------+---------+ 10320
        GCGTCCTTTCTTGTACACTCGTTTTCCGGTCGTTTTCCGGTCCTTGGCATTTTTCCGGCG

GTTGCTGGCGTTTTTCCATAGGCTCCGCCCCCCTGACGAGCATCACAAAAATCGACGCTC
10321   ---------+---------+---------+---------+---------+---------+ 10380
        CAACGACCGCAAAAAGGTATCCGAGGCGGGGGGACTGCTCGTAGTGTTTTTAGCTGCGAG
```

Fig. 1 W

```
       AAGTCAGAGGTGGCGAAACCCGACAGGACTATAAAGATACCAGGCGTTTCCCCCTGGAAG
10381  ---------+---------+---------+---------+---------+---------+  10440
       TTCAGTCTCCACCGCTTTGGGCTGTCCTGATATTTCTATGGTCCGCAAAGGGGGACCTTC

CTCCCTCGTGCGCTCTCCTGTTCCGACCCTGCCGCTTACCGGATACCTGTCCGCCTTTCT
10441  ---------+---------+---------+---------+---------+---------+  10500
       GAGGGAGCACGCGAGAGGACAAGGCTGGGACGGCGAATGGCCTATGGACAGGCGGAAAGA

CCCTTCGGGAAGCGTGGCGCTTTCTCATAGCTCACGCTGTAGGTATCTCAGTTCGGTGTA
10501  ---------+---------+---------+---------+---------+---------+  10560
       GGGAAGCCCTTCGCACCGCGAAAGAGTATCGAGTGCGACATCCATAGAGTCAAGCCACAT

GGTCGTTCGCTCCAAGCTGGGCTGTGTGCACGAACCCCCCGTTCAGCCCGACCGCTGCGC
10561  ---------+---------+---------+---------+---------+---------+  10620
       CCAGCAAGCGAGGTTCGACCCGACACACGTGCTTGGGGGGCAAGTCGGGCTGGCGACGCG

CTTATCCGGTAACTATCGTCTTGAGTCCAACCCGGTAAGACACGACTTATCGCCACTGGC
10621  ---------+---------+---------+---------+---------+---------+  10680
       GAATAGGCCATTGATAGCAGAACTCAGGTTGGGCCATTCTGTGCTGAATAGCGGTGACCG

AGCAGCCACTGGTAACAGGATTAGCAGAGCGAGGTATGTAGGCGGTGCTACAGAGTTCTT
10681  ---------+---------+---------+---------+---------+---------+  10740
       TCGTCGGTGACCATTGTCCTAATCGTCTCGCTCCATACATCCGCCACGATGTCTCAAGAA

GAAGTGGTGGCCTAACTACGGCTACACTAGAAGGACAGTATTTGGTATCTGCGCTCTGCT
10741  ---------+---------+---------+---------+---------+---------+  10800
       CTTCACCACCGGATTGATGCCGATGTGATCTTCCTGTCATAAACCATAGACGCGAGACGA

GAAGCCAGTTACCTTCGGAAAAAGAGTTGGTAGCTCTTGATCCGGCAAACAAACCACCGC
10801  ---------+---------+---------+---------+---------+---------+  10860
       CTTCGGTCAATGGAAGCCTTTTTCTCAACCATCGAGAACTAGGCCGTTTGTTTGGTGGCG

TGGTAGCGGTGGTTTTTTGTTTGCAAGCAGCAGATTACGCGCAGAAAAAAAGGATCTCA
10861  ---------+---------+---------+---------+---------+---------+  10920
       ACCATCGCCACCAAAAAAACAAACGTTCGTCGTCTAATGCGCGTCTTTTTTTCCTAGAGT

AGAAGATCCTTTGATCTTTTCTACGGGGTCTGACGCTCAGTGGAACGAAAACTCACGTTA
```

Fig. 1 X

```
                 TCTTCTAGGAAACTAGAAAAGATGCCCCAGACTGCGAGTCACCTTGCTTTTGAGTGCAAT
10921 ---------+---------+---------+---------+---------+---------+ 10980
                 AGGGATTTTGGTCATGAGATTATCAAAAAGGATCTTCACCTAGATCCTTTTAAATTAAAA

AGGGATTTTGGTCATGAGATTATCAAAAAGGATCTTCACCTAGATCCTTTTAAATTAAAA
10981 ---------+---------+---------+---------+---------+---------+ 11040
                 TCCCTAAAACCAGTACTCTAATAGTTTTTCCTAGAAGTGGATCTAGGAAAATTTAATTTT

ATGAAGTTTTAAATCAATCTAAAGTATATATGAGTAAACTTGGTCTGACAGTTACCAATG
11041 ---------+---------+---------+---------+---------+---------+ 11100
                 TACTTCAAAATTTAGTTAGATTTCATATATACTCATTTGAACCAGACTGTCAATGGTTAC

CTTAATCAGTGAGGCACCTATCTCAGCGATCTGTCTATTTCGTTCATCCATAGTTGCCTG
11101 ---------+---------+---------+---------+---------+---------+ 11160
                 GAATTAGTCACTCCGTGGATAGAGTCGCTAGACAGATAAAGCAAGTAGGTATCAACGGAC

ACTCCCCGTCGTGTAGATAACTACGATACGGGAGGGCTTACCATCTGGCCCCAGTGCTGC
11161 ---------+---------+---------+---------+---------+---------+ 11220
                 TGAGGGGCAGCACATCTATTGATGCTATGCCCTCCCGAATGGTAGACCGGGGTCACGACG

AATGATACCGCGAGACCCACGCTCACCGGCTCCAGATTTATCAGCAATAAACCAGCCAGC
11221 ---------+---------+---------+---------+---------+---------+ 11280
                 TTACTATGGCGCTCTGGGTGCGAGTGGCCGAGGTCTAAATAGTCGTTATTTGGTCGGTCG

CGGAAGGGCCGAGCGCAGAAGTGGTCCTGCAACTTTATCCGCCTCCATCCAGTCTATTAA
11281 ---------+---------+---------+---------+---------+---------+ 11340
                 GCCTTCCCGGCTCGCGTCTTCACCAGGACGTTGAAATAGGCGGAGGTAGGTCAGATAATT

TTGTTGCCGGGAAGCTAGAGTAAGTAGTTCGCCAGTTAATAGTTTGCGCAACGTTGTTGC
11341 ---------+---------+---------+---------+---------+---------+ 11400
                 AACAACGGCCCTTCGATCTCATTCATCAAGCGGTCAATTATCAAACGCGTTGCAACAACG

CATTGCTACAGGCATCGTGGTGTCACGCTCGTCGTTTGGTATGGCTTCATTCAGCTCCGG
11401 ---------+---------+---------+---------+---------+---------+ 11460
                 GTAACGATGTCCGTAGCACCACAGTGCGAGCAGCAAACCATACCGAAGTAAGTCGAGGCC

TTCCCAACGATCAAGGCGAGTTACATGATCCCCCATGTTGTGCAAAAAAGCGGTTAGCTC
11461 ---------+---------+---------+---------+---------+---------+ 11520
```

Fig. 1 Y

```
          AAGGGTTGCTAGTTCCGCTCAATGTACTAGGGGGTACAACACGTTTTTTCGCCAATCGAG

CTTCGGTCCTCCGATCGTTGTCAGAAGTAAGTTGGCCGCAGTGTTATCACTCATGGTTAT
11521  ---------+---------+---------+---------+---------+---------+  11580
          GAAGCCAGGAGGCTAGCAACAGTCTTCATTCAACCGGCGTCACAATAGTGAGTACCAATA

GGCAGCACTGCATAATTCTCTTACTGTCATGCCATCCGTAAGATGCTTTTCTGTGACTGG
11581  ---------+---------+---------+---------+---------+---------+  11640
          CCGTCGTGACGTATTAAGAGAATGACAGTACGGTAGGCATTCTACGAAAAGACACTGACC

TGAGTACTCAACCAAGTCATTCTGAGAATAGTGTATGCGGCGACCGAGTTGCTCTTGCCC
11641  ---------+---------+---------+---------+---------+---------+  11700
          ACTCATGAGTTGGTTCAGTAAGACTCTTATCACATACGCCGCTGGCTCAACGAGAACGGG

GGCGTCAATACGGGATAATACCGCGCCACATAGCAGAACTTTAAAAGTGCTCATCATTGG
11701  ---------+---------+---------+---------+---------+---------+  11760
          CCGCAGTTATGCCCTATTATGGCGCGGTGTATCGTCTTGAAATTTTCACGAGTAGTAACC

AAAACGTTCTTCGGGGCGAAAACTCTCAAGGATCTTACCGCTGTTGAGATCCAGTTCGAT
11761  ---------+---------+---------+---------+---------+---------+  11820
          TTTTGCAAGAAGCCCCGCTTTTGAGAGTTCCTAGAATGGCGACAACTCTAGGTCAAGCTA

GTAACCCACTCGTGCACCCAACTGATCTTCAGCATCTTTTACTTTCACCAGCGTTTCTGG
11821  ---------+---------+---------+---------+---------+---------+  11880
          CATTGGGTGAGCACGTGGGTTGACTAGAAGTCGTAGAAAATGAAAGTGGTCGCAAAGACC

GTGAGCAAAAACAGGAAGGCAAAATGCCGCAAAAAAGGGAATAAGGGCGACACGGAAATG
11881  ---------+---------+---------+---------+---------+---------+  11940
          CACTCGTTTTTGTCCTTCCGTTTTACGGCGTTTTTTCCCTTATTCCCGCTGTGCCTTTAC

TTGAATACTCATACTCTTCCTTTTTCAATATTATTGAAGCATTTATCAGGGTTATTGTCT
11941  ---------+---------+---------+---------+---------+---------+  12000
          AACTTATGAGTATGAGAAGGAAAAAGTTATAATAACTTCGTAAATAGTCCCAATAACAGA

CATGAGCGGATACATATTTGAATGTATTTAGAAAAATAAACAAATAGGGGTTCCGCGCAC
12001  ---------+---------+---------+---------+---------+---------+  12060
          GTACTCGCCTATGTATAAACTTACATAAATCTTTTTATTTGTTTATCCCCAAGGCGCGTG
```

Fig. 1 Z

```
        ATTTCCCCGAAAAGTGCCACCTGACGTCTAAGAAACCATTATTATCATGACATTAACCTA
12061   ---------+---------+---------+---------+---------+---------+ 12120
        TAAAGGGGCTTTTCACGGTGGACTGCAGATTCTTTGGTAATAATAGTACTGTAATTGGAT

TAAAAATAGGCGTATCACGAGGCCCTTTCGTCTCGCGCGTTTCGGTGATGACGGTGAAAA
12121   ---------+---------+---------+---------+---------+---------+ 12180
        ATTTTTATCCGCATAGTGCTCCGGGAAAGCAGAGCGCGCAAAGCCACTACTGCCACTTTT

CCTCTGACACATGCAGCTCCCGGAGACGGTCACAGCTTGTCTGTAAGCGGATGCCGGGAG
12181   ---------+---------+---------+---------+---------+---------+ 12240
        GGAGACTGTGTACGTCGAGGGCCTCTGCCAGTGTCGAACAGACATTCGCCTACGGCCCTC

CAGACAAGCCCGTCAGGGCGCGTCAGCGGGTGTTGGCGGGTGTCGGGGCTGGCTTAACTA
12241   ---------+---------+---------+---------+---------+---------+ 12300
        GTCTGTTCGGGCAGTCCCGCGCAGTCGCCCACAACCGCCCACAGCCCCGACCGAATTGAT

TGCGGCATCAGAGCAGATTGTACTGAGAGTGCACCATATGCGGTGTGAAATACCGCACAG
12301   ---------+---------+---------+---------+---------+---------+ 12360
        ACGCCGTAGTCTCGTCTAACATGACTCTCACGTGGTATACGCCACACTTTATGGCGTGTC

ATGCGTAAGGAGAAAATACCGCATCAGGCGCCATTCGCCATTCAGGCTGCGCAACTGTTG
12361   ---------+---------+---------+---------+---------+---------+ 12420
        TACGCATTCCTCTTTTATGGCGTAGTCCGCGGTAAGCGGTAAGTCCGACGCGTTGACAAC

GGAAGGGCGATCGGTGCGGGCCTCTTCGCTATTACGCCAGCTGGCGAAAGGGGGATGTGC
12421   ---------+---------+---------+---------+---------+---------+ 12480
        CCTTCCCGCTAGCCACGCCCGGAGAAGCGATAATGCGGTCGACCGCTTTCCCCCTACACG

TGCAAGGCGATTAAGTTGGGTAACGCCAGGGTTTTCCCAGTCACGACGTTGTAAAACGAC
12481   ---------+---------+---------+---------+---------+---------+ 12540
        ACGTTCCGCTAATTCAACCCATTGCGGTCCCAAAAGGGTCAGTGCTGCAACATTTTGCTG

GGCCAGTGCC
12541   ---------+ 12550
        CCGGTCACGG
```

Fig. 2:
A
B
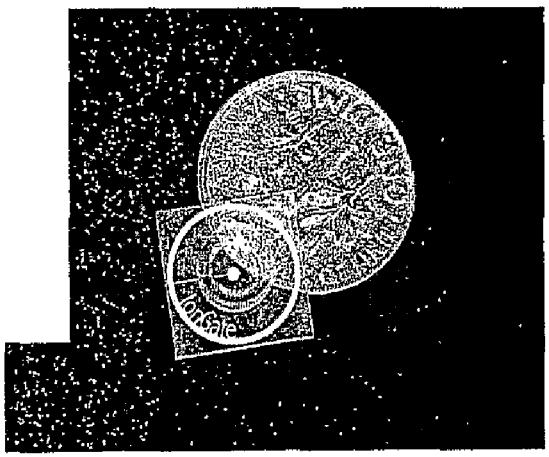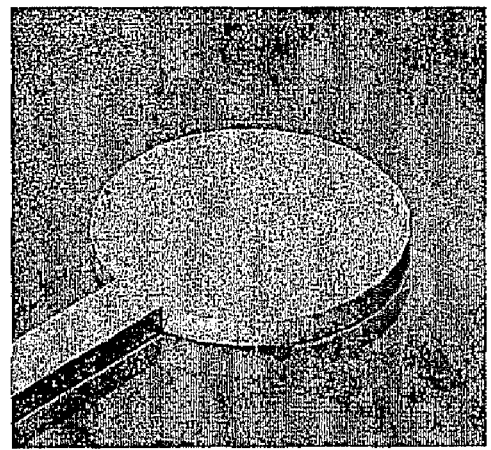
C
D
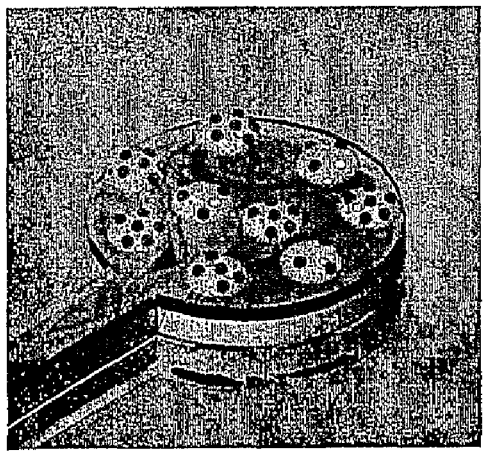

Fig. 3:
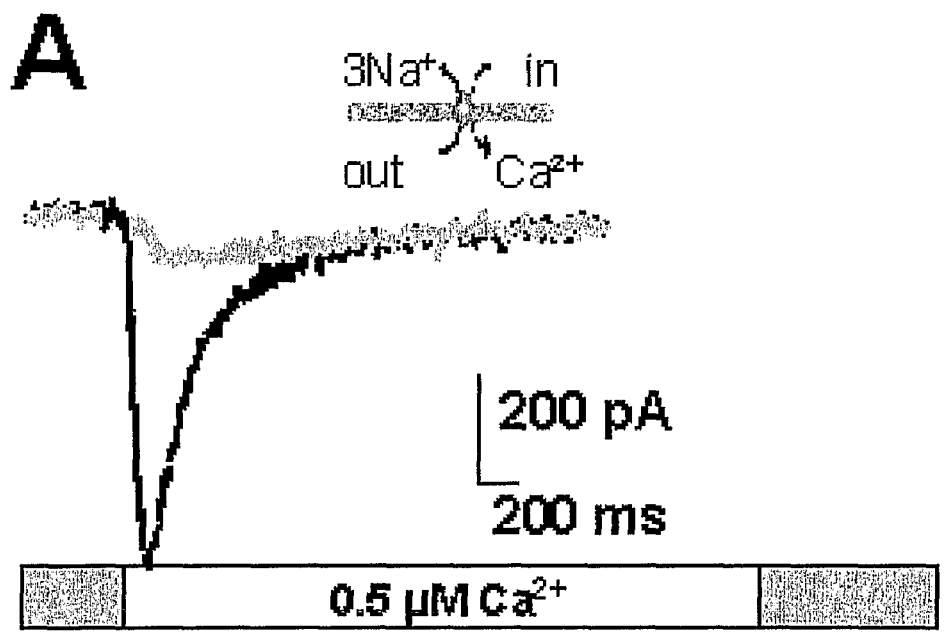
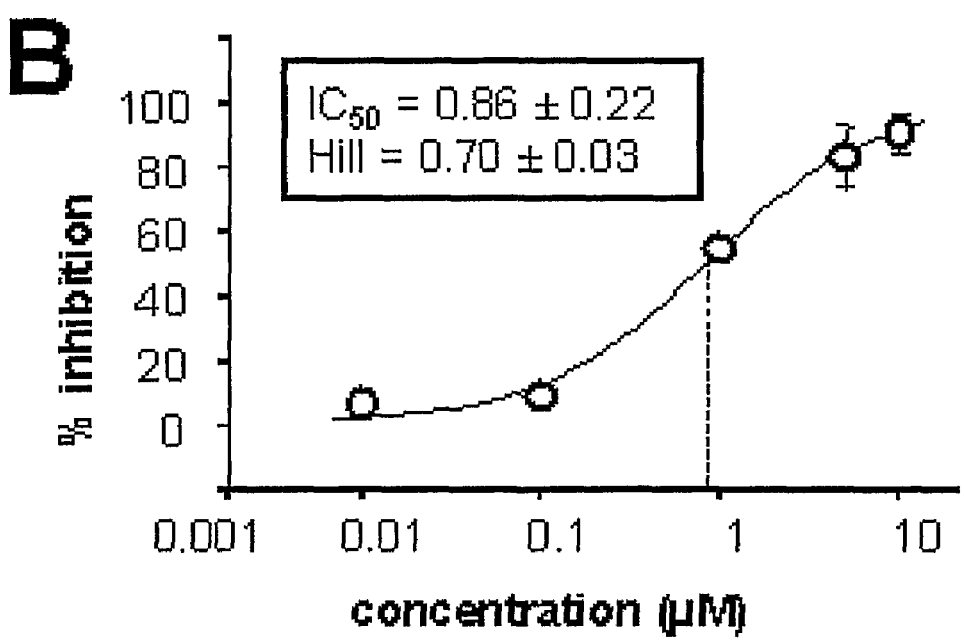

PROCESS FOR IDENTIFICATION OF COMPOUNDS FOR MODULATING THE ACTIVITY OF SODIUM/CALCIUM EXCHANGE TRANSPORTER

The invention refers to a cell free assay for determining the activity or the modulation of the activity of a $Na^+/Ca^{2+}$ exchanger (NCX) protein by means of a cell free electrophysiological sensor chip, a kit of parts comprising the sensor chip with a NCX protein as well as the manufacturing and use of the kit of parts.

GENERAL

A basic requirement for life is compartmentalization—with biological membranes being nature's tool to realize this principle. However, a lipid bilayer—the structure underlying the cell membrane—is impermeable to most ions and compounds whose transport is essential to sustain vital functions in cells and organisms. The answer to this paradox lies in the semi-permeable nature of the cell membrane—solutes that have to cross the membrane are transported by specific membrane proteins. These transporters are responsible for the generation and maintenance of ion gradients, the uptake of nutrients, the transport of metabolites, the reuptake of signaling molecules and the disposal of toxic and waste compounds. Therefore, transporters are potential drug targets that allow direct influence on disease-related abnormalities in this context.

Most membrane transporters shift electrical charges while going through their transport cycle. This shift may originate either from the movement of charged substrates or from the movement of protein moieties carrying (partial) charges.
Monitoring of Transporter-Related Current In some cases the transporter-related currents can either be directly monitored in a rather physiological environment by patch-clamp experiments or at artificial "black lipid membranes". In the latter case, a lipid bilayer is generated in a small hole between two buffer reservoirs, each of them containing an Ag/AgCl electrode. After incorporation of the protein into the bilayer, the biological activity (e.g. enzymatic activity) can be triggered e.g. by photoactivation of ATP derivatives. Yet, due to its lack of stability, no rapid buffer exchange experiments can be conducted with this system, limiting the system to photoactivatable substrates. The lack of stability can be overcome by immobilizing protein-containing particles on a sensor surface. This fact is the rational behind a cell free electrophysiological technology called SurfE²R® (Surface Electrogenic Event Reader) of IonGate Biosciences GmbH, Frankfurt/Main that detects the resulting transporter-related currents.

In analogy also according to the present invention a sensor chip consists of a substrate carrying the transducer and a cover plate with a hole, forming a well similar to those of titer plates. Either glass or polymer plates serve as suitable substrates. In the case of a glass plate, the transducer consists of a thin, lithographically structured gold film which has been chemically modified (e.g. by means of mercaptane) on its surface, whereas with polymer substrates modified thick film gold electrodes can also be used. Due to the range of suitable substrates, single sensor chips can be manufactured as well as sensor strips or even sensor array plates with 96 or 384 sensors. Particularly the polymer-based sensors bear the potential for low cost mass production. Specific examples are disclosed in WO02/074983 and DE10244129.

According to WO 02/074983, the sensor chip described includes a sensor arrangement for pharmacological testing of an active site and/or active ingredient using amperometric and/or potentiometric means (a) with a secondary carrier (20) which has an electrically conductive and solid-like electrode area (21), (b) with a plurality of primary carriers (10) which are located in the immediate spatial vicinity of the secondary carrier (20) and which have biological units (12), especially membrane proteins, which can be activated into electrical action, and (c) with an aqueous measurement medium (30) which contains the primary carriers (10) and the secondary carriers (20), wherein the electrode area (21) is made electrically insulated relative to the measurement medium (30), the electrode area (21) is made electrically insulated relative to the primary carriers (10) and relative to the biological units (12), and the primary carrier (10) can be a eukaryotic cell, a procaryotic cell, a bacterium, a virus, or components, especially membrane fragments, or associations thereof in native form or in altered form, especially in purified, microbiologically and/or molecular biologically altered form, or the primary carrier (10) can be a vesicle, a liposome or a micellar structure.

Moreover, also encompassed by aspects of the present invention is a device for pharmacological testing of an active site and/or active ingredient using amperometric and/or potentiometric means (a) with at least one measurement area (50) in which there is a sensor arrangement (1) as the measurement probe as identified above, (b) with a data acquisition/control means (40) which is made at least for acquiring the measurement data of the sensor arrangement (1) and (c) with an exchange and mixing means (60) which is made for making available, exchanging, mixing and/or adjusting the measurement medium (30).

As further description of the sensor chips, the devices as shown in the FIGS. 4 and 5 are incorporated herein from WO02/074983 FIGS. 1 and 2.

FIG. 4 shows in a schematic and partially cutaway side view of an embodiment of the device for pharmacological testing of an active ingredient. The measurement area 50 in the form of an essentially closed vessel together with an exchange/mixing means 60, for example in the form of a perfusor system or a pump system, forms a closed liquid circuit. Communication of the liquid which is used as the measurement medium 30 takes place via the corresponding feed and drain means 51 and 52. The measurement medium 30 can be an aqueous electrolyte solution here, which has certain ion portions, a given temperature, a certain pH value, etc. Furthermore, in the measurement medium 30 optionally certain substrate substances S and/or certain active ingredients W are contained, or they are added in later process steps by the exchange/mixing means 60. In the measurement area 50 there is a sensor arrangement 1 as referred to above. The sensor arrangement 1 consists of primary carriers 10 which are attached to the surface area 24a of the sensor electrode means 20 which is used as the secondary carrier. In the embodiment shown in FIG. 4 in schematic form and not to scale there is only a single primary carrier 10. It consists of a lipid vesicle or liposome in the form of a lipid double layer or lipid membrane 11 which is made essentially hemispherical and closed. As the essentially biological unit 12 a membrane protein extending through the membrane is inserted into this lipid double layer 11 of the vesicle which is used as the primary carrier 10. By conversion of a substrate S as in the case shown in FIG. 4 which is present in the measurement medium 30 into a converted substrate S' certain processes are initiated in the membrane protein 12 and in the case shown in FIG. 4 lead to transport of the substances of one species Q from the extravesicular side or outside 10a of the vesicle 10 to the intravesicular side or inside 10b of the vesicle 10. If the species Q contains an electrical charge, transport of this species Q from the side 10a to the side 10b leads to net charge transport which corresponds to an electrical current from the outside 10a of the vesicle 10 to the inside 10b of the vesicle 10. On the one hand, in each vesicle 10 generally a host of essentially identical membrane protein molecules 12 in essentially the same orientation in the membrane 11 of the vesicle 10 are incorporated. If they are activated essentially simultaneously—for example by a concentration jump which is initiated by mixing, in the concentration of the substrate S from a nonactivating measurement medium N, 30 without a substrate S to an activating measurement medium A, 30 with the substrate S, this leads to a measurable electrical current. This charge carrier transport is therefore measurable because a host of primary carriers 10 or vesicles are attached to the surface 24a of the sensor electrode means 20 so that upon activation of a host of protein molecules 12 in a host of vesicles in front of the surface 24a of the sensor electrode means 20 a space charge of a certain polarity forms. The space charge then acts on the electrode 26 which in the case shown in FIG. 4 is vapor deposited onto the glass carrier 22 in the form of a gold layer and is covered by a double layer which is used as the insulating area 24 and which consists of a lower layer 24b and an upper layer 24a which is used as the surface and is electrically insulated relative to the measurement medium 30. The surface or the upper layer 24a of the insulation area 24 is for example a lipid monolayer which is compatible with the lipid double layer 11 of the vesicle 10 and which is formed by means of a self-assembling process on an alkane thiol monolayer which forms the lower layer 24b, so that the sequence of layers 24b and 24a, specifically the sequence of an alkane thiol monolayer and a lipid monolayer on a gold substrate formed like a solid as the electrode 26, forms a membrane structure SSM which is also called a solid supported membrane (SSM). Via a connecting line 48i the sensor arrangement 1 and especially the sensor electrode means 20 are connected to a data acquisition/control means 40. The latter has a measurement means 44 in which an electrical current I(t) or an electrical voltage U(t) can be measured as a function of time. Furthermore there is an amplifier means 42 in which the measurement signals are filtered and/or amplified. Via a control line 48s the testing of the active ingredient is controlled by controlling the exchange/mixing means 60. Via another line 48o the electrical circuit is closed by means of an opposing electrode 46, for example in the form of a Pt/Pt electrode or by means of an Ag/AgCl electrode. Insulation 28, 27 and 47 prevents short circuits of the SSM or the opposing electrode 46 relative to the measurement medium 30.

FIG. 5 shows in a schematic and partially cutaway side view an embodiment of the sensor arrangement 1 as shown in FIG. 4 in which instead of a vesicle or liposome the primary carrier 10 is a membrane fragment into which a membrane protein which is used as the biological unit 12 is inserted in an oriented manner. With reference to the embodiment of FIG. 5 it can also be recorded that the figure is not to scale, and on the other hand generally a large plurality of membrane fragments are attached or adsorbed at the same time on the SSM or the surface 24a of the sensor electrode means 20 which is used as the secondary carrier. Here it is also shown again that by conversion of the substrate S which is provided in the measurement medium 30 into a converted substrate S' the transport of the substance of the species Q from one side 10a of the membrane fragment 10 to the opposing side 10b takes place and can be detected as a function of time via the corresponding net charge transport and the associated displacement current.

It holds true for all sensor types that the gold surface is turned into a capacitor after the surface modification has taken place and the well has been filled with an aqueous solution. The properties of this capacitor can be determined by the aid of a current-carrying reference electrode such as Pt/Pt or Ag/AgCl or indium tin oxide (ITO) or others brought in contact with the solution. Furthermore, the sensor surface is very hydrophilic, i.e. sticky for membrane fragments and vesicles. Electrogenic proteins kept within their native or native-like environment, i.e. biological membrane sheets, vesicles or proteoliposomes readily adsorb to the hydrophilic sensor surface, forming compartments whose inner space with its solution is electrically isolated from both, the gold surface as well as the surrounding solution within the well. If inserted into a cuvette, the well of the chip (FIG. 2A) defines the inner volume of a flow cell, enabling a rapid solution exchange above the sensor surface.

Switching from a solution which does not contain a substrate of the investigated protein to a solution that does, induces a measurable, transient charging current of the above mentioned capacitor which is typically within the range of 100 pA to 4 nA.

In the used workstation all components necessary for carrying out solution exchange experiments are accommodated in a PC- or otherwise controlled workstation. In the conventional system, the non-activating (i.e. substrate-free) solution as well as the activating solution are stored in glass bottles. Air pressure applied to the bottles drives the solution through a system of electromechanically operated valves and through the flow cell. Alternatively, an autosampler can be used to process several solutions in a automated fashion.

$Na^+/Ca^{2+}$ Exchanger (NCX)

The term "NCX protein" or "NCX" in context of the present invention shall mean any one of the list of the following $Na^+/Ca^{2+}$ exchanger proteins either alone or in combination with each other: NCX1, NCX2, NCX3, NCX4, NCX5, NCX6, NCX7. Especially preferred are NCX1, NCX2 and/or NCX3. Such NCX protein could be derived from any vertebrate and in particular mammalian species (e.g. dog, horse, bovine, mouse, rat, canine, rabbit, chicken, anthropoid, human or others). The NCX could be isolated from tissue probes of such vertebrate organisms or could be manufactured by means of recombinant biological material that is able to express the NCX protein.

The term "biological material" means any material containing genetic information and capable of reproducing itself or being reproduced in a biological system. Recombinant biological material is any biological material that was produced, has been changed or modified by means of recombinant techniques well known to a person skilled in the art.

The following references are examples of the cloning of particular NCX proteins: The canine $Na^+/Ca^{2+}$ exchanger NCX1 has been cloned by Nicoll, D A. et al. (Science. 250 (4980): 562-5, 1990; Title: Molecular cloning and functional expression of the cardiac sarcolemmal Na(+)-Ca2+ exchanger.). The human $Na^+/Ca^{2+}$ exchanger NCX1 has been cloned by Komuro, I., et al. (Proc. Natl. Acad. Sci. U.S.A. 89 (10), 4769-4773, 1992; Title: Molecular cloning and characterization of the human cardiac Na+/Ca2+ exchanger cDNA) and by Kofuji, P. et al. (Am. J. Physiol. 263 (Cell Physiol. 32): C1241-C1249, 1992; Title: Expression of the Na—Ca exchanger in diverse tissues: a study using the cloned human cardiac Na—Ca exchanger). The human $Na^+/Ca^{2+}$ exchanger NCX2 has been cloned by Li, Z. et al. (J. Biol. Chem. 269 (26): 17434-9, 1994; Title: Cloning of the NCX2 isoform of the plasma membrane Na(+)-Ca2+ exchanger). The rat $Na^+/Ca^{2+}$ exchanger NCX3 has been cloned by Nicoll, D A. et. al.

(J. Biol. Chem. 271(40): 24914-21.1996; Title: Cloning of a third mammalian Na+-Ca2+ exchanger, NCX3). The human Na$^+$/Ca$^{2+}$ exchanger NCX3 has been cloned by Gabellini, N. et. al. (Gene. 298: 1-7, 2002; Title: The human SLC8A3 gene and the tissue-specific Na+/Ca2+ exchanger 3 isoforms).

The Sodium/Calcium exchanger is an important mechanism for removing Ca$^{2+}$ from diverse cells. In heart, it extrudes Ca$^{2+}$ that has entered through Ca$^{2+}$ channels to initiate contraction. Its relevance in cardiovascular diseases is e.g. illustrated in Hobai, J A & O'Rourke, B (2004) Expert Opin. Investig. Drugs, 13, 653-664. Therefore, pharmaceutical industry has developed compounds inhibiting the NCX as e.g. described in Iwamoto, T. et al. (2004) J. Biol. Chem., 279, 7544-7553. The Na$^+$/Ca$^{2+}$ exchanger electrogenically transports three to four Na$^+$ for every Ca$^{2+}$ that moves in the opposite direction as e.g. shown by electrophysiological means in Hinata, M. et al. (2002) J. Physiol. 545, 453-461. The NCX is able to maintain the cytoplasmic Ca$^{2+}$ concentration ([Ca$^{2+}$]$_{in}$) three to four orders of magnitude below the extracellular Ca$^{2+}$ concentration ([Ca$^{2+}$]$_{out}$). Nevertheless, the direction of net Ca$^{2+}$ transport depends on the electrochemical gradient of Na$^+$. Simultaneous and consecutive transport models have been suggested for Na$^+$ and Ca$^{2+}$ translocations, and a bulk of evidence favors the latter.

It is known from the state of the art that the NCX protein's activity can be determined by means of living cells. For this purpose the protein has to be expressed in cells and the cells have to be propagated. Such a system has been disclosed e.g. by Axxam S.r.l. (Mailand, Italy) during the "Pharmaconference 2003" in Pontresina on Poster Nr. P25 (Title: Application of FLIPR platform to study K$^+$ dependent Na$^+$/Ca$^{2+}$ exchangers). These K$^+$ dependent Na$^+$/Ca$^{2+}$ exchangers are different from NCX proteins since they have been isolated from eye's tissue, exhibit a different transport mechanism and are not found expressed in heart tissue. There are further measuring methods known for electrochemical determination of Na$^+$/Ca$^{2+}$ symport systems in cells or in cellular assays. The disadvantage of such systems is that the protein activity has to be determined before a complex biological background containing a mixture of all sorts of macromolecules with potency of interfering with an assay to be applied. The Na$^+$ and Ca$^{2+}$ efflux and influx currents are driven by several and different proteins. The measurement concerning one single protein is, therefore spoiled by a large background. A method free of that disadvantage is a method for electrochemical determination of Na$^+$/Ca$^{2+}$ symport systems in proteo-liposomes (Eisenrauch, A. et al.; J. Membrane Biology (1995) 145: 151-164; Title: Electrical Currents generated by a partially purified Na/Ca exchanger from lobster muscle reconstituted into liposomes and adsorbed on black lipid membranes: activation by photolysis of Ca$^{2+}$). The clear disadvantage of that method would be that no rapid exchange of solutions could happen.

The system of the present invention avoids these disadvantages with respect to the NCX protein by fixing the protein onto a device outside of a cell's background allowing for rapid solution exchange. The activity of the protein is determined then by measurement of a current. Furthermore, a rapid solution exchange is possible.

Therefore, one subject-matter of the present invention refers to an assay for determining the activity of a NCX protein wherein a sensor chip comprising NCX protein is treated stepwise consecutively by washing, non-activating and activating and then the current is measured when changing from non-activating to activating treatment.

The term "sensor chip" means a cell free electrophysiological sensor chip as for example described in WO02/ 074983, in particular in the claims and/or FIGS. 1 and/or 2 including the description of the figures of said PCT application, which is hereby incorporated by reference, if not otherwise described in the present invention.

In particular, this assay comprises a protocol which allows efficient preparation membranes containing NCX protein, a protocol for efficient preparation of sensor chips containing a NCX protein as well as a solution exchange protocol allowing for measuring NCX activity.

In general, the NCX protein used was of mammalian origin, as described above, and in particular of human origin. The NCX protein is elected from NCX1, NCX2, NCX3, NCX4, NCX5, NCX6 and/or NCX7, in particular NCX1, NCX2 and/or NCX3. In a preferred embodiment the NCX protein is a human NCX1 protein. Such NCX proteins could be manufactured by means of recombinant methods known to a person skilled in the art, hereinafter referred to as "recombinant NCX protein" or harvested from native tissue probes, hereinafter referred to as "native NCX protein".

In a preferred embodiment the sensor chip contains a basic body of borofloate-glass that carries gold structures. Further the sensor chip can be preferably covered by a mercaptane layer and having one or several insulating layers. Such a sensor chip (e.g. Borofloate glass chip with rounded gold structures (1-3 mm diameter) and a contact area) is commercially available from IonGate Biosciences GmbH, Industriepark Höchst, D 528, D-65926 Frankfurt am Main, Germany.

A particularly preferred protocol is as follows:

10-30 μl, for example, of NCX-containing membrane fragments were applied and circulated on the sensor chip and preferably incubated for at least 12 hours at 4° C. In preferred cases of experiments the NCX protein is a human NCX1 protein. The capacitance of the protein-loaded sensor chip was preferably around 100 nF cm$^{-2}$ and the conductance G$_{1s}$ preferably around 10 nS cm$^{-2}$. The principal of the assay is to test the electrical activity of NCX protein in the absence of the inhibitor and afterwards in the presence of the inhibitor. For this reason the NCX-sensor chip is rinsed with a sequence of solutions, which activate NCX. In general, there is the possibility to test whether an inhibitor is reversible. In this case after the inhibitor application the solutions are changed back to inhibitor-free conditions. Before the experiment the solution reservoirs of the chip are filled with the following preferred solutions: washing buffer: 40 mM KCl, 100 mM NaCl, 4 mM MgCl$_2$, 30 mM HEPES/NMG pH 7.4; non-activating solution: 140 mM KCl, 4 mM MgCl$_2$, 30 mM HEPES/NMG pH 7.4; activating solution: 140 mM KCl, 4 mM MgCl$_2$, 30 mM HEPES/NMG pH 7.4, 0.5 mM CaCl$_2$. For measurements with inhibitor all three solutions contained the inhibitor in the same concentration. The change from the non-activating to the activating solution leads to the activation of NCX causing a negative current, which decays to the base line. If the average amplitude of NCX-signal in the three measurement cycles is constant, the solutions are changed to the inhibitor-containing solutions and the same protocol is repeated. Afterwards the solutions can be changed back to inhibitor-free conditions, to test whether the inhibitor is reversible.

The term "current" in context of this invention shall mean the peak current in response to the replacement of non-activating by activating solution, including but not limited to the maximal peak current. The current amplitude rises within 10 to 100 ms, followed by a slower decay within about 2 seconds. The polarity of the current may be positive or negative, depending on the polarity of the transported ions and/or the polarity of the shifted moieties of the protein and the vectorial orientation of their transport or shift across or within the membranes of the compartments. Currents resulting from the replacement of the activating solution by non-activating solution or from the replacement of the non-activating solution by the washing solution are not taken into consideration with respect to the determination of the NCX activity. Flow rates and intervals are chosen such that the current response to the replacement of the non-activating solution by activating solution remains unbiased by current responses provoked by the other replacement steps.

The replacing of the washing solution by the non-activating solution will preferably induce a $Na^+$-gradient across membranes harboring NCX protein. Thereafter, replacement of the non-activating solution by activating solution (i.e. $Ca^{2+}$-containing solution) will selectively trigger the NCX activity. Replacing solutions subsequently in reverse order returns the sensor chip into its initial state.

Washing of the sensor chip means generally incubation of the sensor chip in a sodium-containing, calcium-free buffer solution (washing solution) causing preferably an accumulation of $Na^+$ in the vesicular compartments. Again, establishing a $Na^+$-gradient across the membrane is performed by replacing the washing solution by a non-activating solution thereby exposing the sensor chip to a rapid variation of the $Na^+$-concentration. The activation of the NCX is preferably performed by replacing the non-activating solution by an activating solution thereby exposing the sensor chip to a rapid variation of the $Ca^{2+}$-concentration.

In another preferred embodiment the invention pertains to an assay for determining the activity of NCX protein wherein a first solution replacement is performed by replacing the washing solution by non-activation solution and/or a second replacement is performed by replacing the non-activating solution by activating solution and/or a third solution replacement is performed by replacing the activating solution by non-activating solution and/or a fourth solution replacement is performed by replacing the non-activating solution by washing solution.

The invention further pertains to an assay for the identification of a compound that modulates the activity of a NCX protein (Screening assay) wherein
a] a sensor chip is provided that comprises NCX protein;
b] a washing solution, a non-activating solution and an activating solution is provided;
c] a washing solution, a non-activating solution and an activating solution is provided which all of these three solutions contain additionally a chemical compound with the same concentration in all of the three solutions;
d] a sensor chip from a] is treated stepwise consecutively by washing solution, non-activating solution, activating solution, non-activating solution and washing solution from b];
e] a current is determined when changing from non-activating to activating solution in d];
f] a sensor chip from e] is treated stepwise consecutively by washing solution, non-activating solution, activating solution, non-activating solution and washing solution from c];
g] a current is determined when replacing the non-activating by activating solution in f];
thereby proving the modulation of the activity of the NCX protein in case the current from e] is of different strength as the current from g].

The consecutive stepwise treatment in steps d), e) and f could be performed in a continuous flow or an almost continuous flow.

Modulation of the activity of the NCX protein could consist of stimulating or inhibiting of the activity of the NCX protein.

The stimulation of activity is demonstrated when the current from e] is larger than the current from g].

The inhibition of activity is demonstrated when the current from e] is smaller than the current from g].

Preferred embodiments of this protocol are already described above, in the following Examples and the claims.

The invention pertains further to a kit of parts comprising
a] a sensor chip comprising NCX protein,
b] a washing solution,
c] a non-activating solution;
d] an activating solution.

Preferred embodiments of this kit are also already described above, in the following Examples and the claims.

The invention pertains further to the manufacturing of a kit of parts as mentioned before wherein a sensor chip is manufactured, the NCX protein is manufactured, the manufactured NCX protein is fixed onto the surface of the sensor chip, a washing solution is manufactured, a non-activating solution is manufactured, an activating solution is manufactured and the sensor chip comprising NCX protein, the washing solution, the non-activating solution, and the activating solution are combined to a kit unit.

The kit unit could consist of one or several parts comprising e.g. notifications for the user.

The invention pertains further to the use of a kit of parts as mentioned before for identifying of a compound that modifies (=inhibits or activates) the activity of a NCX protein or of determining the activity of NCX1 protein.

The invention pertains further to an assay for determining the activity of NCX protein wherein a sensor chip comprising adsorbed NCX protein containing membranes is exposed to a rapid change in the concentration of at least one NCX substrate (e.g. $Ca^{2+}$ or $Na^+$).

The following Figures and Examples shall describe the invention in further details without limiting the scope of protection.

DESCRIPTION OF THE FIGURES

FIG. 1:
FIG. 1 shows the polynucleotide sequence of vector pVL1393 harboring the cDNA sequence of human NCX1. The according open reading frame is marked by exhibiting the related amino acid sequences. The depicted sequence corresponds to SEQ ID NO: 1. DNA of pVL1393 harboring cDNA for the human NCX1 has been deposited with DSMZ (Deutsche Sammlung für Mikroorganismen and Zellkulturen GmbH; Mascheroder Weg 1b; D-38124 Braunschweig) under DSM 16588.
SEQ ID NO: 1: Polynucleotide sequence of pVL1393
Deposited Biological Material:
DSM 16588: DNA of pVL1393 harboring cDNA for the human NCX1
DSM ACC2670: Flp-In-T-Rex-293-NCX!

Deposits were carried out by transferring the biological material to DSMZ (Deutsche Sammlung für Mikroorganismen und Zellkulturen GmbH; Mascheroder Weg 1b; D-38124 Braunschweig) according to the rules of the Budapest Treaty.

FIG. 2:
A) A 3 mm biosensor chip with gold structure and fluid compartment B-D) Scheme of the biosensors sandwich structure assembly B) gold surface C) coating with chemical linker and lipid D) adsorption of the membranes FIG. 3:
A) Electrical charging current induced by ion transport activity of the recombinantly expressed $Na^+/Ca^{2+}$-exchanger.

B) $IC_{50}$ of a $Na^+/Ca^{2+}$-exchanger inhibitor as acquired with the cell free electrophysiological sensor chip in accordance with the present invention. All errors are quoted as standard error of mean (SEM).

Figure 4:
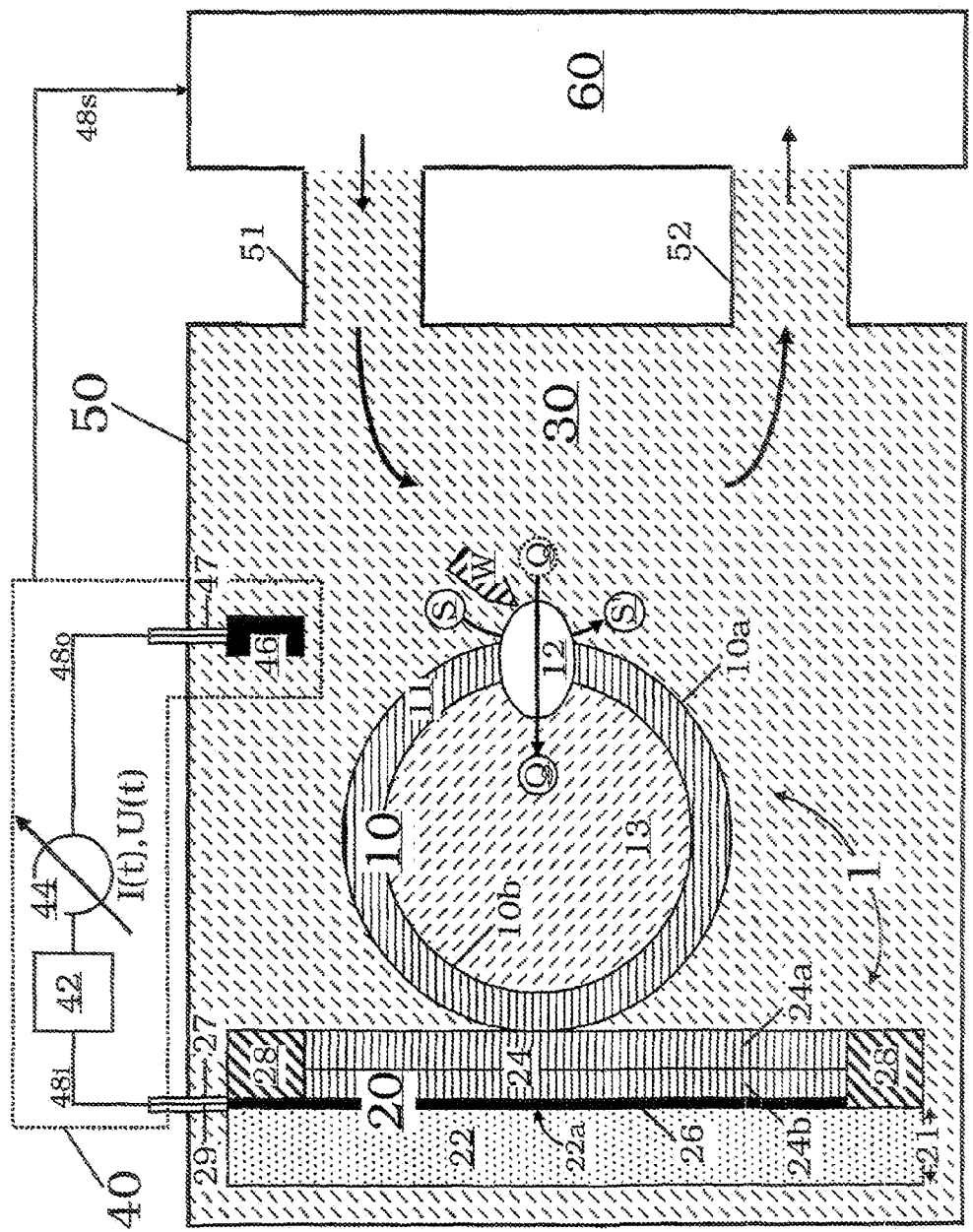

FIG. 4 shows in a schematic and partially cutaway side view of an example sensor chip.

Figure 5:
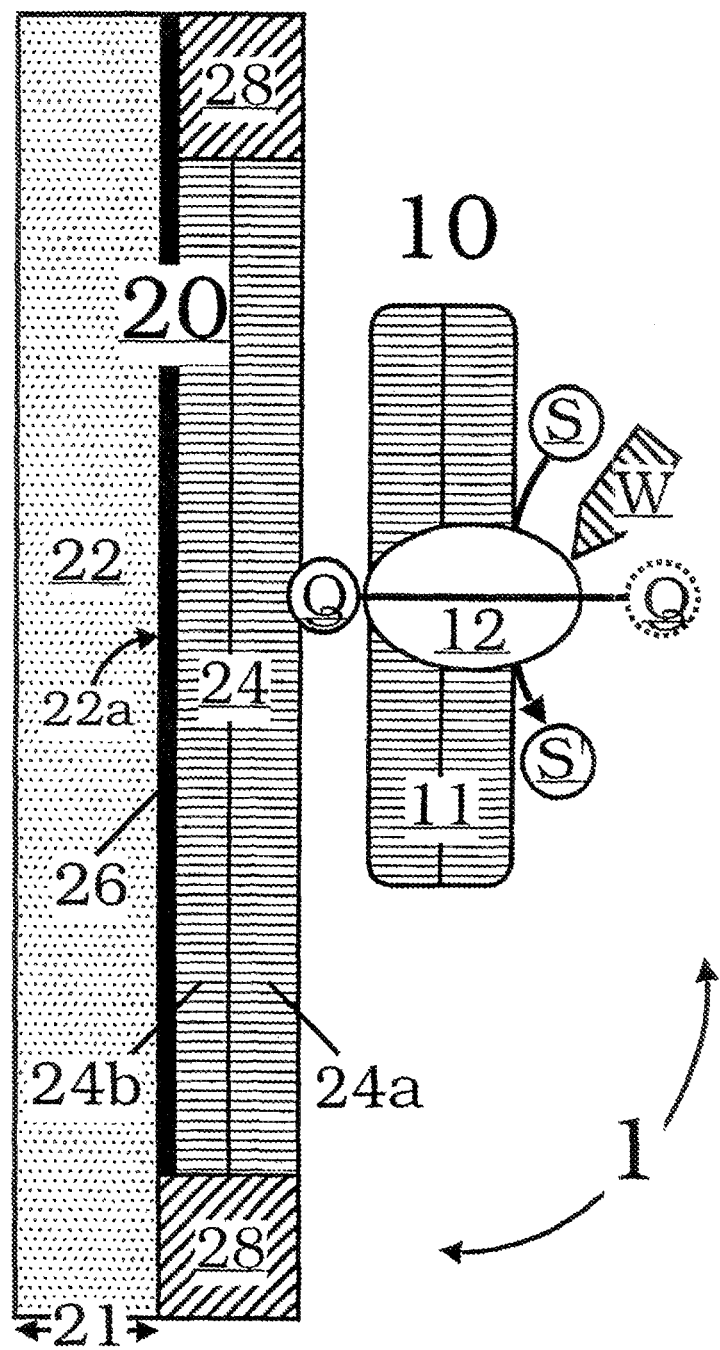

FIG. 5 shows an embodiment of a sensor arrangement with a membrane fragment into which a membrane protein which is used as a biological unit 12 is inserted in an oriented manner.

EXAMPLES

1. Mammalian Cell Line Generation

Rapid generation of stably transfected cell lines was achieved utilizing the Flp-In™ T-Rex™ expression system (Invitrogen Corporation, 1600 Farraday Avenue, Post Box 6482 Carlsbad, Calif. 92008, USA). For this purpose cDNA encoding for the (human) cardiac sodium calcium exchanger (NCX-1, i.e., SLC8A1 PDB-entry NM_021097) was cloned into the Flp-In™ T-Rex™ expression vector (Invitrogen Corporation, 1600 Farraday Avenue, Post Box 6482 Carlsbad, Calif. 92008, USA) and subsequently transfected into HEK-293 cells. The cells were kept in culture under standard conditions (37° C., air supplemented with 8% CO2) in D-MEM (Invitrogen Corporation, 1600 Farraday Avenue, Post Box 6482 Carlsbad, Calif. 92008, USA) supplemented with 10% fetal calf serum (Biochrom AG, Post Box 46 03 09, 12213 Berlin, Germany), 50 mg/ml Hygromycin (Invitrogen Corporation, 1600 Farraday Avenue, Post Box 6482 Carlsbad, Calif. 92008, USA) and 10 mg/ml Blasticidin (Invitrogen Corporation, 1600 Farraday Avenue, Post Box 6482 Carlsbad, Calif. 92008, USA).

Cells were passed every 3 to 4 days using a Trypsin/EDTA solution Biochrom AG, Post Box 46 03 09, 12213 Berlin, Germany) to detach the cells. At least 12 to 24 hours prior to a membrane preparation cells were treated with 1 µg/ml Doxicycline (Beckton Diccinson Bioscience Clontech, 1290 Terra Bella Avenue Mountain View, Calif. 94043, USA) to boost NCX expression.

The Flp-In-T-Rex-293-NCX1 cell line expressing NCX-1 is deposited at DSMZ (Deutsche Gesellschaft von Mikroorganismen und Zellkulturen GmbH; Mascheroder Weg 1b, D-38124 Braunschweig) under DSM ACC2670.

2. Insect Cell Line Generation

Rapid generation of transiently transfected cell lines was achieved utilizing the Bac3000 expression system (EMD Biosciences, Inc., Novagen Brand, 441 Charmany Drive, Madison, Wis. 53719, USA). For this purpose cDNA encoding for the (human) cardiac sodium calcium exchanger (NCX-1, i.e., SLC8A1 PDB-entry NM_021097) was cloned into the Bac3000 expression vector (EMD Biosciences, Inc., Novagen Brand, 441 Charmany Drive, Madison, Wis. 53719, USA). After generating virus according to the manufactures procedures viral stock in an threefold excess was used to transfect Sf9 insect cell. The cells were kept in culture under standard conditions (27° C.) in appropriate medium. Membranes were harvested after 3 days posttransfection. The stock cell culture was maintained according to manufactures procedures.

Specifically, the method can be carried out as follows:
2.1 Co-Transfection to Prepare Recombinant Virus For co-transfection approximately 10 µg of highly purified and sterile plasmid DNA should be prepared. To provide cells for the co-transfection a six-well plate is set up for each transfection as well as for the positive and negative control. 1×10e6 cells Sf9 cells in serum-free medium are seeded on each cavity. Cells are allowed to attach, usually for one hour. While cells are attaching the transfection mix can be prepared, which consists of 15 µl BacVector 3000 from Novagen [0.02 µg/µl], 30 µl Cellfectin (InVitrogen), 0.4 µg recombinant donor plasmid DNA pVL_NCX1 and distilled water ad 50 µl. The incubation time takes 20 min. at room temperature. After this time 0.5 ml medium is added to each mix. If the cells are attached the old medium is removed and the transfection mix is added drop-by drop to the cavity. After 4 h, 27° C. incubation time 1 ml fresh medium (containing 10% serum) is added and another incubation follows for 0.4-5 days at 27° C.

2.2 Plaque-Purification to Isolate a Monoclonal Recombinant Virus Clone

After these 5 days the supernatant of the co-transfection plates is collected (so called virus stock VS0). For the identification of recombinant virus by plaque screening another six-well plate is set up with 1×10E-6 Sf9 cells for each cavity. Cells should settle for at least 30 min. Meanwhile virus is diluted to 1 ml aliquots at dilutions of 10E-3, 10E-4, 10E-5, 10E-6 and 10E-7. After cells have attached well to the plates the media is aspirated off. Quickly 1 ml of diluted virus is added to each well of the 6-well plate. The plates are transferred to a rocking platform and slowly rocked for at least a couple hours. Now the overlay agarose with low melting agarose is prepared (just before use). The following mix is used: 1 part 2× Grace's Medium supplemented with 20% Fetal Calf Serum and 1 part 3% SeaPlaque Agarose in ddH2O. The agarose is completely melted in a microwave. The 1:1 mixture is placed in a 38° C. water bath. Now all the medium is aspirated off from the cavities and 1 ml overlay mix is added to each well by allowing it to slide down the far wall of the well and onto the plate. After overlaying the cells, the plates stay for 30 minutes in the hood. After this time 1 ml medium is added to each cavity to avoid drying up. The plates are placed in a 27° C., 98% humidity controlled incubator for at least 3 days.

After this the plaques are stained with a solution of 1 ml 1% Neutral red. to each well of a 6-well dish. Plates are returned to the incubator for at least 4 hours. During this time the plaques will begin to appear as clear spots among stained cells. With a sterile pasteur pipette one plaque (ore more) is picked and transferred into a 25 cm² T-flask with 2e6 Sf9 cells in total and a culture volume of 4 ml with 5% FCS. Incubation follows for 5-6 days at 27° C. The culture supernatant is collected (so called virus stock VS1) and used for the next step: the determination of the virus titer.

2.3. Plaque Assay for Virus Titer Determination

Same procedure as described under 2.2.

The plaques are counted and the titer is calculated by using the following equation (for example 20 plaques are counted)

$$\text{Titer (pfu/ml)} = 20 \text{ plaques at } 10E\text{-}6 \times \left(\frac{1}{1 \text{ ml inoculum/well}}\right)$$

Titer (pfu/ml) = $2 \times 10e7$ pfu/ml (plaque forming units/ml)

2.4. Amplification of the Recombinant Virus in a Larger Scale (i.e. 1 L)

For the virus amplification usually a M.O.I. (multiplicity of infection) of 0.1 is used, that means a ratio of 1 virus for 10 Sf9 cells. Since the virus has the possibility for secondary infection cycles the amplification time should be approximately 7 days. During this time the virus will be amplified exponentially and the vitality of the cell culture can decrease to 20-30%. For generating high virus titer a 5% FCS supplementation is recommended and the use of a super-spinner culture vessel with bubble-free aeration. After one week the culture supernatant is collected (so called virus stock VS2). This is a larger volume of virus stock which is sufficient for several expression studies and which can be stored for several month (up to 1 year) at 4° C. and light protected.

2.5. Expression of the Recombinant Protein NCX1

For all expression experiments a M.O.I of 3 is recommended (ratio: 3 virus particles for 1 Sf9 cell) and an incubation time of 72 h, at 27° C.

3. Membrane/Protein Preparation

Cells from native tissue or recombinant expression systems were harvested by mechanical separation of the surrounding environments (bottle or body) surface.

Membrane fragments were prepared by cell rapture and subsequent centrifugation steps and/or sucrose gradient centrifugation.

Specifically, the method can be carried out as follows:

3.1 Insect Cell Membrane/Protein Preparation

After harvesting the cells via centrifugation and aliquots of approx. 2 g wet weight cells from Sf9 suspension culture are quick-frozen in liquid Nitrogen and stored at −80° C. for further preparation.

The cell pellet is thawed on ice and transferred to ice-cold buffer (0.25M sucrose, 5 mM Tris pH 7.5, 2 mM DTT, one complete protease inhibitor cocktail tablet per 50 ml (Roche Diagnostics GmbH, Mannheim, Germany).

The membrane fragments were prepared by cell rapture. Cells are homogenized by the nitrogen cell disruption method utilizing a Parr Cell Disruption Bomb (Parr Instrument Company, Ill., USA) or the Dounce homogenisation method utilizing a Dounce Homogenisator (7 ml from Novodirect GmbH, Kehl/Rhein, Germany) and the suspension centrifuged 10 min at 4° C. and 680 g. The supernatants are collected and again centrifuged for 1 h at 4° C. and 10000 g in SW41 swing-out rotor.

Pellets are suspended in approximately 2 ml of 5 mM Tris pH 7.5. With 87% sucrose (in 5 mM Tris) the suspension is adjusted to 56%. The sucrose gradient is now built up beginning with 2 ml of the 56% fraction at the bottom, following 3 ml 45% sucrose, 3 ml 35% and 2 ml 16% sucrose.

Again centrifugation for 2.5 h (or even more) at 4° C. and 100000 g the gradient-bands are aspirated carefully with a pasteur pipette and collected in fresh tubes together with 5 ml of 100 mM NaCl, 1.5 mM EDTA, 40 mM Hepes pH 7.5.

Another centrifugation step follows: 30 min 150000 g, 4° C.

The resulting pellet is resuspended in 100 mM NaCl, 1.5 mM EDTA, 2 mM DTT, 40 mM Hepes pH 7.5, 10% glycerol.

4. Sensor Chip Preparation

The chip comprises the NCX protein in all instances the protein sticks or is attached to the chip. This may occur e.g. by hydrophobic, hydrophilic, ionic or covalent forces.

The sensor chip of such an assay consists e.g. of a basic body of borofloate glass that carries gold structures. This device would be further covered by a mercaptane layer and having one or several insulating layers.

In a preferred embodiment the borofloatee glass with gold structures was coated with a mercaptane layer and a lipid film consisting of 60 weight units of, 2-Diphytanoyl-sn-Glycero-3-Phosphocholin (AVANTI 850 356) and 1 weight unit of octadecylamine (FLUKA) dissolved in 800 weight units n-decane (in detail: 150 µl PC (Stock 20 mg/ml in hexane or $CHCl_3$ as distributed by AVANTI+10 µl octadecylamine (5 mg/ml in hexane) are evaporate with nitrogen, and taken up in 400 µl n-decane.). To achieve this the sensor chip was incubated with 30 µL mercaptane for 15 min and then washed with isopropanol (3×70 µL) and vacuum dried. After several hours 2 µL lipide+30 µL DTT-buffer (2 mM, 1,542 mg DTT/50 mL Puffer C) was pipetted on top of the sensor chip and incubated for 20 min. To create a functional sensor chip 10 µL of the membrane of interest+120 µL DTT-Puffer was mixed and the ultrasonicated 2×10 units (0.5/30) with a 30 s break on ice. The buffer is then removed from the sensor chip and replaced by 30 µL membrane containing buffer, which is pipetted up and down and stored at least for 12 h at 4° C.

5. Solution Exchange Protocol

For the determination of its activity, the NCX protein was treated consecutively with a washing, non-activating and activating solution and the electrical current was measured when changing from charging to activating treatment. The replacement of the pre-incubation solution (sodium-containing, calcium-free buffer solution) with the charging solution (reduced sodium, calcium-free buffer solution) induces a $Na^+$-gradient across membranes harboring NCX protein. Thereafter, replacement of the solution by activating solution ($Ca^{2+}$-containing solution) triggers the NCX activity. Subsequently replacing solutions in reverse order returns the sensor chip into its initial state.

After buffer containers A, B, and C of the biosensor system had been filled with "activating" buffer (30 mM HEPES/NMG pH 7.4, 140 mM KCl, 4 mM $MgCl_2$, 0.5 mM $CaCl_2$.), "non-activating" buffer (30 mM HEPES/NMG pH 7.4, 140 mM KCl, 4 mM $MgCl_2$), and "washing" buffer (30 mM HEPES/NMG pH 7.4, 40 mM KCl, 100 mM NaCl, 4 mM $MgCl_2$) respectively, a dummy was mounted to the sensor holder and the system was flushed with all buffers to remove air bubbles from the entire fluidic system. An empty or blind sensor was then replaced by a standard glass-based sensor preloaded with NCX1-containing HEK membrane fragments (chemically modified gold surface of 3 mm diameter; Ion-Gate Biosciences GmbH, Frankfurt/M., Germany). Liquid transport through the fluidic system, including the sensor flow cell, was achieved by applying air pressure to the buffer containers.

Measurements were usually carried out at 200 mbar overpressure, resulting in a flow rate of about 300 µl $s^{-1}$. For the determination of its activity, the membranes harboring NCX protein were treated consecutively by an "washing," "non-activating" and "activating" solution. The replacement of the "washing" solution by the "non-activating" solution induces a $Na^+$-gradient across membranes harboring NCX protein. Thereafter, replacement of the "non-activating" solution by "activating" solution triggers the NCX activity and thus the induced electrical current was measured when changing from "non-activating" to "activating" treatment. Subsequently replacing solutions in reverse order returns the sensor chip into its initial state. By means of the control software, a sequence was defined in which "washing" buffer flowed over the sensor surface for 0.5 s, followed by "non-activating" buffer (2.0 s), "activating" buffer (2.0 s), "non-activating" buffer (2.0 s), and "washing" buffer (2.0 s). During the whole sequence, the current response was digitized (2000 samples $s^{-1}$) and saved to data files. For dose-response experiments inhibitors were dissolved in "activating," "non-activating" and "activating" buffer, respectively. All chemicals were of analytical grade or better.

The following settings are used for the measurements of NCX1:

| Cycle 1: | | | | | |
|---|---|---|---|---|---|
| washing buffer | non-activating solution | activating solution | non-activating solution | washing buffer | break |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 1 |

5 minutes break

| Cycle 2: | | | | | |
|---|---|---|---|---|---|
| washing buffer | non-activating solution | activating solution | non-activating solution | washing buffer | break |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 1 |

5 minutes break and addition of a compound to be analyzed

| Cycle 3: | | | | | |
|---|---|---|---|---|---|
| Washing buffer | non-activating solution | activating solution | non-activating solution | washing buffer | break |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 1 |

5 minutes break

| Cycle 4: | | | | | |
|---|---|---|---|---|---|
| Washing buffer | non-activating solution | activating solution | non-activating solution | washing buffer | break |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 42 |
| 0.5 s | 2 s | 2 s | 2 s | 4 s | 1 |

5 minutes break and addition of the same compound in another concentration or of another compound, etc.

6. Experiment

Due to the protocol the NCX-containing membrane fragments bound to the biosensors surface are exposed to a rapid $Ca^{2+}$ concentration jump leading to a transient charging current (FIG. 3a). It should be noted again, that a particular preference for this experimental outcome is an extra-vesicular $Na^+$ reduction applied directly before the experiment to the biosensor to generate a sodium gradient. The reason for the fast decay of the current is due to inactivation and/or capacitive coupling of the transporter to the surface of the membrane fragments. In effect, a stationary current charges the sandwich structure of the biosensor and therefore generates an electrical field that allows charging only to a limited state—similar to an DC current source charging a capacitor.

FIG. 3 A shows a typical cell-free electrophysiological NCX biosensor recording before (black trays) and after (grey trays) inhibition with a NCX-specific inhibitor. A biosensor subjected to rapid Ca concentration jumps, in the absence or presence of 10 μM inhibitor A in all solutions generated a NCX peak current of 300 pA or 20 pA respectively, showing the specificity of the signal. The application of 10 μM of the inhibitor resulted in a decrease of the NCX-specific signal of 90.5%±5.1% (n=5) The resulting dose-response curve is shown in FIG. 3B. $IC_{50}$ values (n=5) were recorded with application of the inhibitors' concentrations of 0.01, 0, 1, 1, 5, and 10 μM. The value for 50% inhibition can be calculated to 0.86 μM±0.22 μM. The Hill coefficient could be calculated to 0.7±0.03. Subsequent experiments in the absence of the inhibitor resulted in NCX peak currents with up to 100% of the amplitude of the initial signal, proving the inhibitors' reversibility.

In control experiments the current could be diminished by reduction of the applied $Ca^{2+}$ jump and by application of the unspecific NCX1 blocker of $Ni^{2+}$ (5 mM). Furthermore, membranes of cells not expressing NCX1 did not yield currents under similar experimental conditions.

The invention claimed is:

1. An in vitro assay for determining the activity of an NCX protein wherein a sensor chip comprising said NCX protein is treated stepwise consecutively with a washing, non-activating and activating solution and the current is measured when changing from non-activating to activating treatment; said sensor chip comprising a body of borosilicate glass or wherein said sensor chip is covered by a mercaptane layer and has one or several insulating layers.

2. The assay as claimed in claim 1 wherein the sensor chip comprises at least one NCX protein selected from the group consisting of: NCX1, NCX2, NCX3, NCX4, NCX5, NCX6, NCX7.

3. The assay as claimed in claim 2 wherein the sensor chip comprises NCX protein of mammalian origin.

4. The assay as claimed in claim 3 wherein the NCX protein is human NCX1 protein.

5. The assay as claimed in claim 1 wherein the sensor chip is a recombinant NCX protein or a native NCX protein.

6. The assay as claimed in claim 1 wherein a first solution replacement is performed by replacing the washing solution by a non-activation solution.

7. The assay as claimed in claim 1 wherein a second replacement is performed by replacing the non-activating solution by an activating solution.

8. The assay as claimed in claim 1 wherein a third solution replacement is performed by replacing the activating solution by a non-activating solution.

9. The assay as claimed in claim 1 wherein a fourth solution replacement is performed by replacing the non-activating solution by a washing solution.

10. An assay for identifying of a compound that modulates activity of a NCX protein wherein
  a] a sensor chip comprising said NCX protein is provided, wherein the sensor chip comprises a body of borofloate-glass that carries gold structures or the sensor chip is covered by a mercaptane layer and wherein the sensor chip has one or several insulating layers;
  b] a washing solution, a non-activating solution and an activating solution are provided;
  c] a washing solution, a non-activating solution and an activating solution are provided which each of these three solutions contains a chemical compound at the same concentration in all of the three solutions;
  d] said sensor chip from a] is treated stepwise consecutively by said washing solution, said non-activating solution, said activating solution, said non-activating solution and said washing solution from b];
  e] a current is determined when changing from said non-activating to said activating solution in d];
  f] said sensor chip from e] is treated stepwise consecutively by said washing solution, said non-activating solution, said activating solution, said non-activating solution and said washing solution from c];
  g] a current is determined when replacing the non-activating by the activating solution in f];
thereby proving modulation of the activity of the NCX protein in case the current from e] is of different strength as the current from g].

11. The assay as claimed in claim 10 wherein the sensor chip comprises at least one of the NCX proteins selected from the group consisting of: NCX1, NCX2, NCX3, NCX4, NCX5, NCX6, NCX7.

12. The assay as claimed in claim 11 wherein the sensor chip comprises NCX protein of mammalian origin.

13. The assay as claimed in claim 12 wherein the NCX protein is human NCX1 protein.

14. The assay as claimed in claim 10 wherein the sensor chip comprises NCX protein that was produced by means of recombinant biological material.

15. A kit of parts comprising:
  a] a sensor chip comprising NCX protein, wherein the sensor chip comprises a body of borofloate-glass that carries gold structures or the sensor chip is covered by a mercaptane layer and harboring one or several insulating layers;
  b] a washing solution;
  c] a non-activating solution; and
  d] an activating solution.

16. The kit of parts as claimed in claim 15 wherein the sensor chip comprises at least one of the NCX proteins selected from the group consisting of: NCX1, NCX2, NCX3, NCX4, NCX5, NCX6, NCX7.

17. The kit of parts as claimed in claim 16 wherein the NCX protein is of mammalian origin.

18. The kit of parts as claimed in claim 17 wherein the NCX protein is human NCX1 protein.

19. The kit of parts as claimed in claim 15 wherein the sensor chip comprises human NCX protein that was produced by means of recombinant biological material.

20. The kit of parts as claimed in claim 15 wherein the washing solution comprises: 30±15 mM HEPES/NMG pH 7.4±1.0; 40±20 mM KCl; 100±50 mM NaCl; and 4±2 mM $MgCl_2$.

21. The kit of parts as claimed in claim 15 wherein the non-activating solution comprises: 30±15 mM HEPES/NMG pH 7.4±1.0; 140±70 mM KCl; and 4±2 mM $MgCl_2$.

22. The kit of parts as claimed in claim 15 wherein the activating solution comprises 30±15 mM HEPES/NMG pH 7.4±1.0; 140±70 mM KCl, 4±2 mM $MgCl_2$; and 0.5±0.25 mM $CaCl_2$.

23. An assay for determining activity of NCX protein wherein a sensor chip containing a body of boro-fluoroate-glass that carries gold structures or a sensor chip being covered by a mercaptane layer and having one or several insulating layers; said sensor chip comprising adsorbed NCX protein containing membranes, is exposed to a rapid change in the concentration of at least one NCX substrate.

24. The assay as claimed in claim 23 wherein the NCX substrate is $Ca^{2+}$ or $Na^+$.

25. The assay as claimed in claim 3 wherein the NCX protein is a mouse, rat or humanroin.

26. The assay as claimed in claim 12 wherein the NCX protein is a mouse, rat or humanroin.

27. The kit of parts as claimed in claim 17 wherein the NCX protein is a mouse, rat or human protein.

* * * * *

SEQUENCE LISTING

<160> NUMBER OF SEQ ID NOS: 1

<210> SEQ ID NO 1
<211> LENGTH: 12550
<212> TYPE: DNA
<213> ORGANISM: Homo Sapiens

<400> SEQUENCE: 1
aagctttact cgtaaagcga gttgaaggat catatttagt tgcgtttatg agataagatt    60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180

-continued

```
gtgactagcg aagaagatgt gtggaccgca gaacagatag taaaacaaaa ccctagtatt    240
ggagcaataa tcgatttaac caacacgtct aaatattatg atggtgtgca ttttttgcgg    300
gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg atattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc ttttcacga    1380 cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680 tatggggaa catgcgccgc tacaacactc gtcgttatga acgcagacgg cgccggtctc    1740
ggcgcaagcg gctaaaacgt gttgcgcgtt caacgcggca aacatcgcaa aagccaatag   1800
tacagttttg atttgcatat taacggcgat ttttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttggggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gttttacga agcgatgaca    2520 tgaccccccgt agtgacaacg atcacgccca aaagaactgc cgactacaaa attaccgagt   2580
```

```
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aatgaaaac tgtcgacaag    3240 ctctgtccgt ttgctggcaa ctgcaagggg ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatattaa    3420 aatcattttc aaatgattca cagttaattt gcgacaatat aattttattt tcacataaac    3480
tagacgcctt gtcgtcttct tcttcgtatt ccttctcttt ttcatttttc tcctcataaa    3540
aattaacata gttattatcg tatccatata tgtatctatc gtatagagta aattttttgt    3600
tgtcataaat atatatgtct tttttaatgg ggtgtatagt accgctgcgc atagtttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat ttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcccgggta    4140
ccttctagac accatgtaca acatgcggcg attaagtctt tcacccacct tttcaatggg    4200
atttcatctg ttagttactg tgagtctctt attttcccat gtggaccatg taattgctga    4260
gacagaaatg gaaggagaag gaaatgaaac tggtgaatgt actggatcat attactgtaa    4320
gaaaggggtg attttgccca tttgggaacc ccaagaccct tcttttgggg acaaaattgc    4380
tagagctact gtgtattttg tggccatggt ctacatgttt cttggagtct ctatcatagc    4440
tgatcggttc atgtcctcta tagaagtcat cacatctcaa gaaaaagaaa taaccataaa    4500
gaaacccaat ggagagacca ccaagacaac tgtgaggatc tggaatgaaa cagtttctaa    4560
cctgaccttg atggccctgg gatcttctgc tcctgagatt ctcctttcag taattgaagt    4620
gtgtggccat aacttcactg caggagacct cggtcctagc accatcgtgg gaagtgctgc    4680
attcaatatg ttcatcatta ttgcactctg tgtttatgtg gtgcctgacg gagagacaag    4740
gaagattaag catttgcgtg tcttctttgt gacagcagcc tggagcatct ttgcctacac    4800
ctggctttac attattttgt ctgtcatatc tcctggtgtt gtggaggtct gggaaggttt    4860
gcttactttc ttcttctttc ccatctgtgt tgtgttcgct tgggtagcgg ataggagact    4920
tctgttttac aagtatgtct acaagaggta tcgagctggc aagcagaggg ggatgattat    4980
```

```
tgaacatgaa ggagacaggc catcttctaa gactgaaatt gaaatggacg ggaaagtggt    5040
caattctcat gttgaaaatt tcttagatgg tgctctggtt ctggaggtgg atgagaggga    5100
ccaagatgat gaagaagcta ggcgagaaat ggctaggatt ctgaaggaac ttaagcagaa    5160
gcatccagat aaagaaatag agcaattaat agaattagct aactaccaag tcctaagtca    5220
gcagcaaaaa agtagagcat tttatcgcat tcaagctact cgcctcatga ctggagctgg    5280
caacatttta aagaggcatg cagctgacca agcaaggaag ctgtcagca tgcacgaggt    5340 caacactgaa gtgactgaaa atgaccctgt tagtaagatc ttctttgaac aagggacata    5400
tcagtgtctg gagaactgtg gtactgtggc ccttaccatt atccgcagag gtggtgattt    5460
gactaacact gtgtttgttg acttcagaac agaggatggc acagcaaatg ctgggtctga    5520
ttatgaattt actgaaggaa ctgtggtgtt taagcctggt gatacccaga aggaaatcag    5580
agtgggtatc atagatgatg atatctttga ggaggatgaa aatttccttg tgcatctcag    5640
caatgtcaaa gtatcttctg aagcttcaga agatggcata ctggaagcca atcatgtttc    5700
tacacttgct tgcctcggat ctccctccac tgccactgta actattttg atgatgacca    5760 cgcaggcatt tttacttttg aggaacctgt gactcatgtg agtgagagca ttggcatcat    5820
ggaggtgaaa gtattgagaa catctggagc tcgaggaaat gttatcgttc catataaaac    5880
catcgaaggg actgccagag gtggagggga ggattttgag gacacttgtg gagagctcga    5940
attccagaat gatgaaattg tcaaaacaat atcagtcaag gtaattgatg atgaggagta    6000
tgagaaaaac aagaccttct tccttgagat tggagagccc cgcctggtgg agatgagtga    6060
gaagaaagcc ctgttattga atgagcttgg tggcttcaca ataacaggaa aatacctgtt    6120
tggccaacct gtcttcagga aggttcatgc tagagaacat ccgattctct ctactgtaat    6180
caccattgca gacgaatatg atgacaagca gccactgacc agcaaagagg aagaggagag    6240
gcgcattgca gaaatggggc gccccatcct gggagagcac accaagttgg aagtgatcat    6300
tgaagaatcc tatgaattca gagtactgtg gacaaactc attaagaaga caaacctggc    6360
ccttgtggtt gggactaaca gctggagaga acagttcatt gaagctatca ctgtcagtgc    6420
tggggaagat gatgacgacg atgaatgtgg ggaagagaag ctgccctcct gtttcgatta    6480
cgtgatgcac tttctgactg tgttctggaa ggtcctgttt gccttcgtcc ccctactga    6540 atactggaat ggctgggcgt gtttcattgt ctccatcctc atgattggcc tactgacagc    6600
tttcattgga gacctggctt cccactttgg ctgcaccatt ggcctgaaag attctgtgac    6660
tgcagtcgtg ttcgtcgcac ttggaacatc agtgccagac acatttgcca gcaaagtggc    6720
agccacccag gaccagtatg cagacgcctc cataggtaac gtcacgggca gcaacgcgt    6780 gaatgtcttc ctgggaatcg gtgtggcctg gccatcgct gccatctacc acgcagccaa    6840 tgggaacag ttcaaagtgt ccctggcac actagctttc tctgtcactc tcttcaccat    6900 ttttgcttc atcaatgtgg gggtgctgct gtatcggcgg aggccagaaa tcggaggtga    6960
gctgggtggg ccccggactg ccaagctcct cacatcctgc ctctttgtgc tcctatggct    7020
cttgtacatt tccttctcct ccctggaggc ctactgccac ataaaaggct tctaagcggc    7080
cgctgcagat ctgatccttt cctgggaccc ggcaagaacc aaaaactcac tctcttcaag    7140
gaaatccgta atgttaaacc cgacacgatg aagcttgtcg ttggatggaa aggaaaagag    7200
ttctacaggg aaacttggac ccgcttcatg gaagacagct tccccattgt taacgaccaa    7260
gaagtgatgg atgtttcct tgttgtcaac atgcgtccca ctagacccaa ccgttgttac    7320
aaattcctgg cccaacacgc tctgcgttgc gaccccgact atgtacctca tgacgtgatt    7380
```

-continued

```
aggatcgtcg agccttcatg ggtgggcagc aacaacgagt accgcatcag cctggctaag    7440
aagggcggcg gctgcccaat aatgaacctt cactctgagt acaccaactc gttcgaacag    7500
ttcatcgatc gtgtcatctg ggagaacttc tacaagccca tcgtttacat cggtaccgac    7560
tctgctgaag aggaggaaat tctccttgaa gtttccctgg tgttcaaagt aaaggagttt    7620
gcaccagacg cacctctgtt cactggtccg gcgtattaaa acacgataca ttgttattag    7680
tacatttatt aagcgctaga ttctgtgcgt tgttgattta cagacaattg ttgtacgtat    7740
tttaataatt cattaaattt ataatcttta gggtggtatg ttagagcgaa aatcaaatga    7800
ttttcagcgt ctttatatct gaatttaaat attaaatcct caatagattt gtaaaatagg    7860
tttcgattag tttcaaacaa gggttgtttt tccgaaccga tggctggact atctaatgga    7920
ttttcgctca acgccacaaa acttgccaaa tcttgtagca gcaatctagc tttgtcgata    7980
ttcgtttgtg ttttgttttg taataaaggt tcgacgtcgt tcaaatatt atgcgctttt    8040
gtatttcttt catcactgtc gttagtgtac aattgactcg acgtaaacac gttaaataaa    8100
gcttggacat atttaacatc gggcgtgtta gctttattag gccgattatc gtcgtcgtcc    8160
caaccctcgt cgttagaagt tgcttccgaa gacgattttg ccatagccac acgacgccta    8220
ttaattgtgt cggctaacac gtccgcgatc aaatttgtag ttgagctttt tggaattatt    8280
tctgattgcg ggcgttttg ggcgggtttc aatctaactg tgcccgattt taattcagac    8340
aacacgttag aaagcgatgg tgcaggcggt ggtaacattt cagacggcaa atctactaat    8400
ggcggcggtg gtggagctga tgataaatct accatcggtg gaggcgcagg cggggctggc    8460
ggcggaggcg gaggcggagg tggtggcggt gatgcagacg gcggtttagg ctcaaatgtc    8520
tctttaggca acacagtcgg cacctcaact attgtactgg tttcgggcgc cgttttggt    8580
ttgaccggtc tgagacgagt gcgattttt tcgtttctaa tagcttccaa caattgttgt    8640
ctgtcgtcta aaggtgcagc gggttgaggt tccgtcggca ttggtggagc gggcggcaat    8700
tcagacatcg atggtggtgg tggtggtgga ggcgctggaa tgttaggcac gggagaaggt    8760
ggtggcggcg gtgccgccgg tataattgt tctggttag tttgttcgcg cacgattgtg    8820
ggcaccggcg caggcgccgc tggctgcaca acggaaggtc gtctgcttcg aggcagcgct    8880
tggggtggtg gcaattcaat attataattg gaatacaaat cgtaaaaatc tgctataagc    8940
attgtaattt cgctatcgtt taccgtgccg atatttaaca accgctcaat gtaagcaatt    9000
gtattgtaaa gagattgtct caagctcgcc gcacgccgat aacaagcctt tcatttta    9060
ctacagcatt gtagtggcga gacacttcgc tgtcgtcgac gtacatgtat gctttgttgt    9120
caaaaacgtc gttggcaagc tttaaaatat ttaaaagaac atctctgttc agcaccactg    9180
tgttgtcgta aatgttgttt tgataatttt gcgcttccgc agtatcgaca cgttcaaaaa    9240
attgatgcgc atcaattttg ttgttcctat tattgaataa ataagattgt acagattcat    9300
atctacgatt cgtcatggcc accacaaatg ctacgctgca aacgctggta caattttacg    9360
aaaactgcaa aaacgtcaaa actcggtata aaataatcaa cgggcgcttt ggcaaaatat    9420
ctatttatc gcacaagccc actagcaaat tgtatttgca gaaaacaatt tcggcgcaca    9480
attttaacgc tgacgaaata aaagttcacc agttaatgag cgaccaccca aatttttataa    9540
aaatctattt taatcacggt tccatcaaca accaagtgat cgtgatggac tacattgact    9600
gtcccgattt atttgaaaca ctacaaatta aaggcgagct ttcgtaccaa cttgttagca    9660
atattattag acagctgtgt gaagcgctca acgatttgca caagcacaat ttcatacaca    9720
acgacataaa actcgaaaat gtcttatatt tcgaagcact tgatcgcgtg tatgtttgcg    9780
```

```
attacggatt gtgcaaacac gaaaactcac ttagcgtgca cgacggcacg ttggagtatt    9840
ttagtccgga aaaaattcga cacacaacta tgcacgtttc gtttgactgg tacgcggcgt    9900
gttaacatac aagttgctaa cgtaatcatg gtcatagctg tttcctgtgt gaaattgtta    9960
tccgctcaca attccacaca acatacgagc cggaagcata aagtgtaaag cctggggtgc   10020
ctaatgagtg agctaactca cattaattgc gttgcgctca ctgcccgctt tccagtcggg   10080
aaacctgtcg tgccagctgc attaatgaat cggccaacgc gcggggagag gcggtttgcg   10140
tattgggcgc tcttccgctt cctcgctcac tgactcgctg cgctcggtcg ttcggctgcg   10200
gcgagcggta tcagctcact caaaggcggt aatacggtta ccacagaat cagggataa    10260 cgcaggaaag aacatgtgag caaaaggcca gcaaaaggcc aggaaccgta aaaaggccgc   10320
gttgctggcg tttttccata ggctccgccc ccctgacgag catcacaaaa atcgacgctc   10380
aagtcagagg tggcgaaacc cgacaggact ataaagatac caggcgtttc ccctggaag   10440 ctccctcgtg cgctctcctg ttccgaccct gccgcttacc ggatacctgt ccgcctttct   10500
cccttcggga agcgtggcgc tttctcatag ctcacgctgt aggtatctca gttcggtgta   10560
ggtcgttcgc tccaagctgg gctgtgtgca cgaaccccc gttcagcccg accgctgcgc    10620
cttatccggt aactatcgtc ttgagtccaa cccggtaaga cacgacttat cgccactggc   10680
agcagccact ggtaacagga ttagcagagc gaggtatgta ggcggtgcta cagagttctt   10740
gaagtggtgg cctaactacg gctacactag aaggacagta tttggtatct gcgctctgct   10800
gaagccagtt accttcggaa aaagagttgg tagctcttga tccggcaaac aaaccaccgc   10860
tggtagcggt ggtttttttg tttgcaagca gcagattacg cgcagaaaaa aaggatctca   10920
agaagatcct ttgatctttt ctacggggtc tgacgctcag tggaacgaaa actcacgtta   10980
agggattttg gtcatgagat tatcaaaaag gatcttcacc tagatccttt taaattaaaa   11040
atgaagtttt aaatcaatct aaagtatata tgagtaaact tggtctgaca gttaccaatg   11100
cttaatcagt gaggcaccta tctcagcgat ctgtctattt cgttcatcca tagttgcctg   11160
actccccgtc gtgtagataa ctacgatacg ggagggctta ccatctggcc ccagtgctgc   11220
aatgataccg cgagacccac gctcaccggc tccagattta tcagcaataa accagccagc   11280
cggaagggcc gagcgcagaa gtggtcctgc aactttatcc gcctccatcc agtctattaa   11340
ttgttgccgg gaagctagag taagtagttc gccagttaat agtttgcgca acgttgttgc   11400
cattgctaca ggcatcgtgg tgtcacgctc gtcgtttggt atggcttcat tcagctccgg   11460
ttcccaacga tcaaggcgag ttacatgatc ccccatgttg tgcaaaaaag cggttagctc   11520
cttcggtcct ccgatcgttg tcagaagtaa gttggccgca gtgttatcac tcatggttat   11580
ggcagcactg cataattctc ttactgtcat gccatccgta agatgctttt ctgtgactgg   11640
tgagtactca accaagtcat tctgagaata gtgtatgcgg cgaccgagtt gctcttgccc   11700
ggcgtcaata cgggataata ccgcgccaca tagcagaact ttaaaagtgc tcatcattgg   11760
aaaacgttct cggggcgaaa actctcaag gatcttaccg ctgttgagat ccagttcgat    11820
gtaacccact cgtgcaccca actgatcttc agcatctttt actttcacca gcgtttctgg   11880
gtgagcaaaa acaggaaggc aaaatgccgc aaaaaaggga ataagggcga cacggaaatg   11940
ttgaatactc atactcttcc ttttcaata ttattgaagc atttatcagg gttattgtct    12000
catgagcgga tacatatttg aatgtattta gaaaaataaa caaatagggg ttccgcgcac   12060
```

-continued

| | | | | | |
|---|---|---|---|---|---|
| atttccccga | aaagtgccac | ctgacgtcta | agaaaccatt | attatcatga | cattaaccta 12120 |
| taaaaatagg | cgtatcacga | ggcccttcg | tctcgcgcgt | ttcggtgatg | acggtgaaaa 12180 |
| cctctgacac | atgcagctcc | cggagacggt | cacagcttgt | ctgtaagcgg | atgccgggag 12240 |
| cagacaagcc | cgtcagggcg | cgtcagcggg | tgttggcggg | tgtcggggct | ggcttaacta 12300 |
| tgcggcatca | gagcagattg | tactgagagt | gcaccatatg | cggtgtgaaa | taccgcacag 12360 |
| atgcgtaagg | agaaaatacc | gcatcaggcg | ccattcgcca | ttcaggctgc | gcaactgttg 12420 |
| ggaagggcga | tcggtgcggg | cctcttcgct | attacgccag | ctggcgaaag | ggggatgtgc 12480 |
| tgcaaggcga | ttaagttggg | taacgccagg | gttttcccag | tcacgacgtt | gtaaaacgac 12540 |
| ggccagtgcc | | | | | 12550 |